(12) United States Patent
Orbay

(10) Patent No.: US 7,744,638 B2
(45) Date of Patent: Jun. 29, 2010

(54) SYSTEM FOR STABILIZATION OF FRACTURES OF CONVEX ARTICULAR BONE SURFACES INCLUDING SUBCHONDRAL SUPPORT STRUCTURE

(75) Inventor: Jorge L. Orbay, Miami, FL (US)

(73) Assignee: Depuy Products, Inc., Warsaw, IN (US)

( * ) Notice: Subject to any disclaimer, the term of this patent is extended or adjusted under 35 U.S.C. 154(b) by 1406 days.

(21) Appl. No.: 11/040,732

(22) Filed: Jan. 21, 2005

(65) Prior Publication Data

US 2005/0182406 A1    Aug. 18, 2005

Related U.S. Application Data

(60) Provisional application No. 60/538,589, filed on Jan. 23, 2004, provisional application No. 60/546,127, filed on Feb. 20, 2004, provisional application No. 60/598,110, filed on Aug. 2, 2004, provisional application No. 60/643,432, filed on Jan. 7, 2005.

(51) Int. Cl.
A61B 17/56 (2006.01)
A61B 17/58 (2006.01)

(52) U.S. Cl. .............. 606/280; 606/70; 606/71; 606/281; 606/282

(58) Field of Classification Search .......... 606/70, 606/71, 280–291, 902–905
See application file for complete search history.

(56) References Cited

U.S. PATENT DOCUMENTS

| | | | |
|---|---|---|---|
| 1,091,674 A | | 3/1914 | Lee |
| 2,077,804 A | | 4/1937 | Morrison |
| 2,500,370 A | * | 3/1950 | McKibbin ............ 606/67 |
| 2,685,877 A | | 8/1954 | Dobelle |
| 3,489,143 A | | 1/1970 | Halloran ............ 128/92 |
| 3,552,389 A | | 1/1971 | Allgower et al. |
| 3,668,972 A | | 6/1972 | Allgower et al. |
| 3,716,050 A | | 2/1973 | Johnston |
| 3,779,240 A | | 12/1973 | Kondo |
| 3,791,380 A | | 2/1974 | Dawidowski |
| RE28,841 E | | 6/1976 | Allgower et al. |

(Continued)

FOREIGN PATENT DOCUMENTS

CH            611147         5/1979

(Continued)

OTHER PUBLICATIONS

Philos, The Anatomical Fixation Sytem for the Proximal Humerus with Angular Stability, XP-002205191, Jan. 1, 2001, pp. 1-3.

(Continued)

*Primary Examiner*—Thomas C Barrett
*Assistant Examiner*—Sameh Boles
(74) *Attorney, Agent, or Firm*—Gordon & Jacobson, PC

(57) ABSTRACT

A fracture fixation system is provided for a fracture of a head portion of a long bone which has subchondral bone defining a convex articular surface, and particularly the proximal humerus. The system includes a plate element positionable on the long bone substantially opposite the head portion of the long bone and on a first side of the fracture, and a post element extending from the plate and into the head portion and across the fracture.

6 Claims, 21 Drawing Sheets

U.S. PATENT DOCUMENTS

| | | | |
|---|---|---|---|
| 4,219,015 A | 8/1980 | Steinemann | |
| 4,408,601 A | 10/1983 | Wenk | |
| RE31,628 E | 7/1984 | Allgower et al. | |
| 4,493,317 A | 1/1985 | Klaue | |
| 4,498,468 A | 2/1985 | Hansson | |
| 4,513,744 A | 4/1985 | Klaue | |
| 4,561,432 A | 12/1985 | Mazor | |
| 4,565,193 A | 1/1986 | Streli | |
| 4,622,959 A | 11/1986 | Marcus | |
| 4,632,101 A | 12/1986 | Freedland | |
| 4,721,103 A | 1/1988 | Freedland | |
| 4,733,654 A | 3/1988 | Marino | |
| 4,794,919 A | 1/1989 | Nilsson | 128/92 |
| 4,838,252 A | 6/1989 | Klaue | |
| 4,858,602 A | 8/1989 | Seidel et al. | 128/92 |
| 4,927,421 A | 5/1990 | Goble et al. | |
| 4,957,118 A | 9/1990 | Erlebacher | |
| 4,957,497 A | 9/1990 | Hoogland et al. | |
| 4,988,350 A | 1/1991 | Herzberg | |
| 5,002,544 A | 3/1991 | Klaue et al. | |
| 5,006,120 A | 4/1991 | Carter | |
| 5,041,114 A | 8/1991 | Chapman et al. | |
| 5,085,660 A | 2/1992 | Lin | |
| 5,127,914 A | 7/1992 | Calderale et al. | |
| 5,129,901 A | 7/1992 | Decoste | |
| 5,151,103 A | 9/1992 | Tepic et al. | |
| 5,160,335 A | 11/1992 | Wagenknecht | |
| 5,180,383 A | 1/1993 | Haydon | 606/72 |
| 5,190,544 A | 3/1993 | Chapman et al. | 606/69 |
| 5,197,966 A | 3/1993 | Sommerkamp | |
| 5,269,784 A | 12/1993 | Mast | |
| 5,275,601 A | 1/1994 | Gogolewski et al. | |
| 5,304,180 A | 4/1994 | Slocum | |
| 5,324,290 A | 6/1994 | Zdeblick et al. | |
| 5,324,291 A | 6/1994 | Ries et al. | |
| 5,364,398 A | 11/1994 | Chapman et al. | |
| 5,364,399 A | 11/1994 | Lowery et al. | |
| 5,458,654 A | 10/1995 | Tepic | 623/23 |
| 5,472,444 A | 12/1995 | Huebner et al. | 606/64 |
| 5,489,284 A | 2/1996 | James et al. | |
| 5,514,138 A | 5/1996 | McCarthy | |
| 5,531,748 A | 7/1996 | de la Caffiniere | |
| 5,578,035 A | 11/1996 | Lin | 606/68 |
| 5,601,553 A | 2/1997 | Trebing et al. | |
| 5,674,222 A | 10/1997 | Berger et al. | |
| 5,676,667 A | 10/1997 | Hausman | 606/69 |
| 5,702,399 A | 12/1997 | Kilpela et al. | |
| 5,709,686 A | 1/1998 | Talos et al. | 606/69 |
| 5,749,872 A | 5/1998 | Kyle et al. | 606/69 |
| 5,759,184 A | 6/1998 | Santangelo | |
| 5,776,194 A | 7/1998 | Mikol et al. | 623/16 |
| 5,797,913 A | 8/1998 | Dambreville et al. | |
| 5,810,823 A | 9/1998 | Klaue et al. | |
| 5,840,078 A | 11/1998 | Yerys | |
| 5,843,127 A | 12/1998 | Li | |
| 5,849,004 A | 12/1998 | Bramlet | |
| 5,882,351 A | 3/1999 | Fox | |
| 5,931,839 A | 8/1999 | Medoff | 606/69 |
| 5,938,664 A | 8/1999 | Winquist et al. | |
| 5,976,139 A | 11/1999 | Bramlet | |
| 5,993,449 A | 11/1999 | Schlapfer et al. | |
| 6,096,040 A | 8/2000 | Esser | 606/69 |
| 6,183,474 B1 | 2/2001 | Bramlet | |
| 6,183,475 B1 | 2/2001 | Lester et al. | |
| 6,206,881 B1 | 3/2001 | Frigg et al. | |
| D443,060 S | 5/2001 | Benirschke et al. | D24/155 |
| 6,270,499 B1 | 8/2001 | Leu et al. | 606/64 |
| 6,287,310 B1 | 9/2001 | Fox | |
| 6,322,562 B1 | 11/2001 | Wolter | |
| 6,358,250 B1 | 3/2002 | Orbay | 606/69 |
| 6,364,882 B1 | 4/2002 | Orbay | 606/69 |
| 6,379,359 B1 | 4/2002 | Dahners | 606/62 |
| 6,406,477 B1 | 6/2002 | Fujiwara | |
| 6,409,768 B1 | 6/2002 | Tepic et al. | 623/23.27 |
| 6,440,135 B2 | 8/2002 | Orbay et al. | 606/69 |
| 6,443,954 B1 | 9/2002 | Bramlet et al. | |
| 6,454,770 B1 | 9/2002 | Klaue | |
| 6,468,278 B1 | 10/2002 | Muckter | 606/69 |
| 6,527,776 B1 | 3/2003 | Michelson | |
| 6,558,388 B1 | 5/2003 | Bartsch et al. | |
| 6,562,042 B2 | 5/2003 | Nelson | |
| 6,579,294 B2 | 6/2003 | Robioneck | |
| D479,331 S | 9/2003 | Pike et al. | |
| 6,623,486 B1 * | 9/2003 | Weaver et al. | 606/281 |
| 6,648,889 B2 | 11/2003 | Bramlet et al. | |
| 6,648,890 B2 | 11/2003 | Culbert et al. | |
| 6,669,701 B2 | 12/2003 | Steiner et al. | |
| 6,685,706 B2 | 2/2004 | Padget et al. | |
| 6,689,135 B2 | 2/2004 | Enayati | |
| 6,706,046 B2 | 3/2004 | Orbay et al. | |
| 6,866,665 B2 | 3/2005 | Orbay | 606/69 |
| 6,926,720 B2 | 8/2005 | Castaneda | |
| 7,282,053 B2 * | 10/2007 | Orbay | 606/291 |
| 7,326,212 B2 * | 2/2008 | Huebner | 606/328 |
| 2002/0156474 A1 | 10/2002 | Wack et al. | |
| 2002/0161369 A1 | 10/2002 | Bramlet | |
| 2003/0004514 A1 | 1/2003 | Frigg et al. | |
| 2005/0010226 A1 | 1/2005 | Grady, Jr. et al. | 606/69 |

FOREIGN PATENT DOCUMENTS

| | | |
|---|---|---|
| DE | 8907443 | 9/1989 |
| DE | G 92 00 328.1 | 4/1992 |
| DE | 43 41 980 A | 6/1995 |
| DE | 43 43 117 A1 | 6/1995 |
| DE | 44 38 264 A1 | 3/1996 |
| DE | 93 21 544 U1 | 10/1999 |
| DE | 19857279 | 6/2000 |
| DE | 29907161 | 8/2000 |
| DE | 20200705 U1 | 3/2002 |
| EP | 0 207 884 A2 | 1/1987 |
| EP | 1 468 655 A2 | 10/2004 |
| FR | 2233973 | 1/1975 |
| FR | 2405062 | 5/1979 |
| FR | 2405705 | 5/1979 |
| FR | 2405706 | 5/1979 |
| FR | 2 606 268 | 5/1988 |
| JP | 04138152 | 5/1992 |
| SU | 1279626 | 12/1986 |
| WO | WO 97/09000 | 3/1997 |
| WO | WO 00/53110 | 9/2000 |
| WO | WO 00/53111 | 9/2000 |
| WO | WO 02/096309 A1 | 12/2002 |
| WO | WO2005/037117 | 4/2005 |

OTHER PUBLICATIONS

Zimmer Periarticular Plating System—Low-Profile Fixation (catalog). Zimmer, Inc., 2003. (8 pages).

The Mayo Clinic Congruent Elbow Plates (catalog). ACUMED. Hillsboro, OR: 2003. (20 pages).

Locking Compression Plate (LCP) System (brochure). SYNTHES. West Chester, PA: 2003. (6 pages).

Hessman et al., "Internal Fixation of Proximal Humeral Fractures: Current Concepts," European Journal of Trauma, 2003 No. 5, p. 253-261.

Osgood and Ahmad, "Two- and Three-Part Fractures of the Proximal Humerus," Shoulder and Elbow Trauma, 2004, Chapter 13, p. 169-182.

* cited by examiner

SYSTEM FOR STABILIZATION OF FRACTURES OF CONVEX ARTICULAR BONE SURFACES INCLUDING SUBCHONDRAL SUPPORT STRUCTURE

CROSS-REFERENCE TO RELATED APPLICATIONS

The application claims the benefit of U.S. Provisional Application 60/538,589, filed Jan. 23, 2004, 60/546,127, filed Feb. 20, 2004, 60/598,110, filed August 2, 2004, and 60/643,432, filed Jan. 7, 2005.

BACKGROUND OF THE INVENTION

1. Field of the Invention

This invention relates broadly to surgical devices. More particularly, this invention relates to a fracture fixation system including an orthopedic plate and associated fasteners for fastening the plate to the bone and tendons.

2. State of the Art

The proximal humerus comprises the upper portion of the humerus, i.e. upper arm of the human body, commonly known as the shoulder area. Fractures of the proximal humerus typically result from traumatic injuries such as sporting accidents and can be more frequent with age due to bone loss. Fractures of the proximal humerus are treated by exposing the fracture site and reducing the bone fracture and then placing a plate or other means onto the bone to fixate the fracture for healing in the reduced position. Reducing the fracture includes realigning and positioning the fractured portions of the bone to their original position or similar stable position. Fixating the fracture includes positioning a plate over the fractured portions and securing the plate onto the fractured bones and adjacent non-fractured bones with bone screws.

Conventional fixation plates have several shortcomings when applied to the proximal humerus. In general, they are not well shaped for the humeral anatomy, and when provided in a size necessary to provide the structural rigidity for stability of a humeral fracture are not easily shaped by the surgeon. Furthermore, such plates require large screws which do not provide purchase in underlying osteoporotic bone.

Two plates particularly contoured for the proximal humerus are the locking proximal humeral plate (LPHP) and PHILOS from Synthes of Paoli, Pa. These plates include a proximal head portion which receives several fixed angle fasteners which extend into the rounded head of the humerus perpendicular to the articular surface and threadably couple to the plate. Particularly in osteoporotic bone, there is a tendency for the fasteners to pierce the bone and enter the articular space between the head of the humerus and the shoulder socket which can cause significant irritation and potentially greater orthopedic damage. Such damage can interfere with, prolong, or prevent proper healing of the humeral fracture, in addition to causing the patient additional pain and the development of post-traumatic arthritis.

SUMMARY OF THE INVENTION

It is therefore an object of the invention to provide a humeral fracture fixation system which is anatomically appropriate for the humerus.

It is another object of the invention to provide a humeral fracture fixation system which provides a stable framework for support of a proximal humeral fracture.

It is a further object of the invention to provide a humeral fracture fixation system in which the fasteners extending through the plate will not break through the articular surface.

It is also object of the invention to provide a humeral fracture fixation system which facilitates alignment of fasteners into the head of the humerus.

It is yet another object of the invention to provide a humeral fracture fixation system which provides the surgeon a tactile sensation of when fasteners are properly implanted within the head of the humerus.

In accord with these objects, which will be discussed in detail below, a humeral fracture fixation system is provided and includes a plate, a plurality of cortical screws, and a plurality of posts for coupling the plate to the humerus and stabilizing the fracture. The system preferably also includes K-wires and suture material, as discussed below.

The plate is provided with a plurality of post holes. A post is provided for each post hole, and extends through the head portion of the plate generally perpendicular to the articular surface of the shoulder. According to a preferred aspect of the invention, a post may be provided with a support means for supporting the subchondral bone of the articular surface. When provided with such support means, the post includes a head which preferably can be fixed in a particular rotational orientation relative to the post hole so that the support means is always oriented in a particular orientation, and preferably in alignment with the anterior-posterior plane, relative to the plate and the anatomy.

According to another preferred aspect of the invention, the head portion includes a plurality of alignment holes which are sized to closely receive individual K-wires in a particular orientation. The orientation of axes through the alignment holes, and consequently K-wires inserted therethrough, closely conforms to the space defined by the posts when coupled to the head portion of the plate.

After the fracture is reduced and prior to drilling holes for the posts, the surgeon drills K-wires through the alignment holes on the head portion of the plate to temporarily fix the orientation of the head of the plate to the head of the humerus. Once the alignment is so fixed, the fracture is examined, e.g., under fluoroscopy, to determine whether the fracture is reduced in an anatomically correct manner and if the K-wires are properly aligned relative to the anatomy. The fluoroscopically viewed K-wires provide an indication as to whether the posts will be properly oriented in relation to the fracture and articular surface. If the placement is correct, the K-wires maintain the position of the plate over the fracture while holes are drilled for the posts. If placement is not optimal, the K-wires can be removed and the surgeon has an opportunity to relocate and/or reorient the K-wires and drill again. Since each K-wire is of relatively small diameter, the bone is not significantly damaged by the drilling process and the surgeon is not committed to the initial drill location and/or orientation. Once the plate is properly positioned with the K-wires, the plate, posts, and support means, if provided, can be implanted, and the K-wires can be removed.

According to yet another preferred aspect of the invention, the head portion includes a lower proximal recess and a plurality of suture guides with holes thereabout. The recess raises the suture guides off the surface of the bone to allow the surgeon to pass a needle with suture material through the suture guides and between the plate and the bone to permit tendon and bone fragments to be sutured to the plate.

With the fixation system implanted, the posts are oriented perpendicular to the articular surface but do not extend far enough to break through the articular surface.

Additional objects and advantages of the invention will become apparent to those skilled in the art upon reference to the detailed description taken in conjunction with the provided figures.

DETAILED DESCRIPTION OF THE PREFERRED EMBODIMENTS

Figure 1:
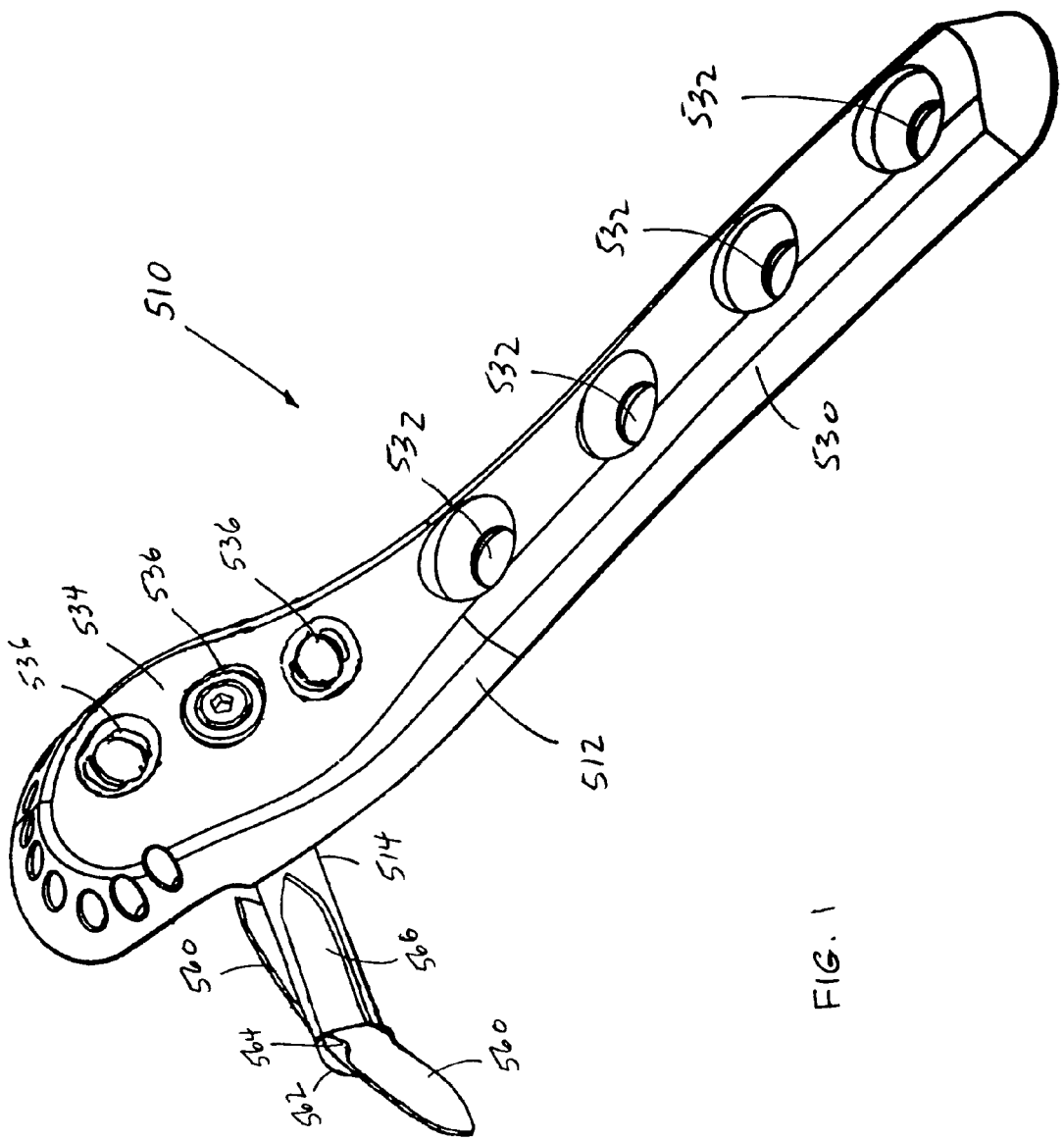
FIG. 1 is a perspective view of an embodiment of a proximal humeral fixation system according to the invention.
Figure 2:
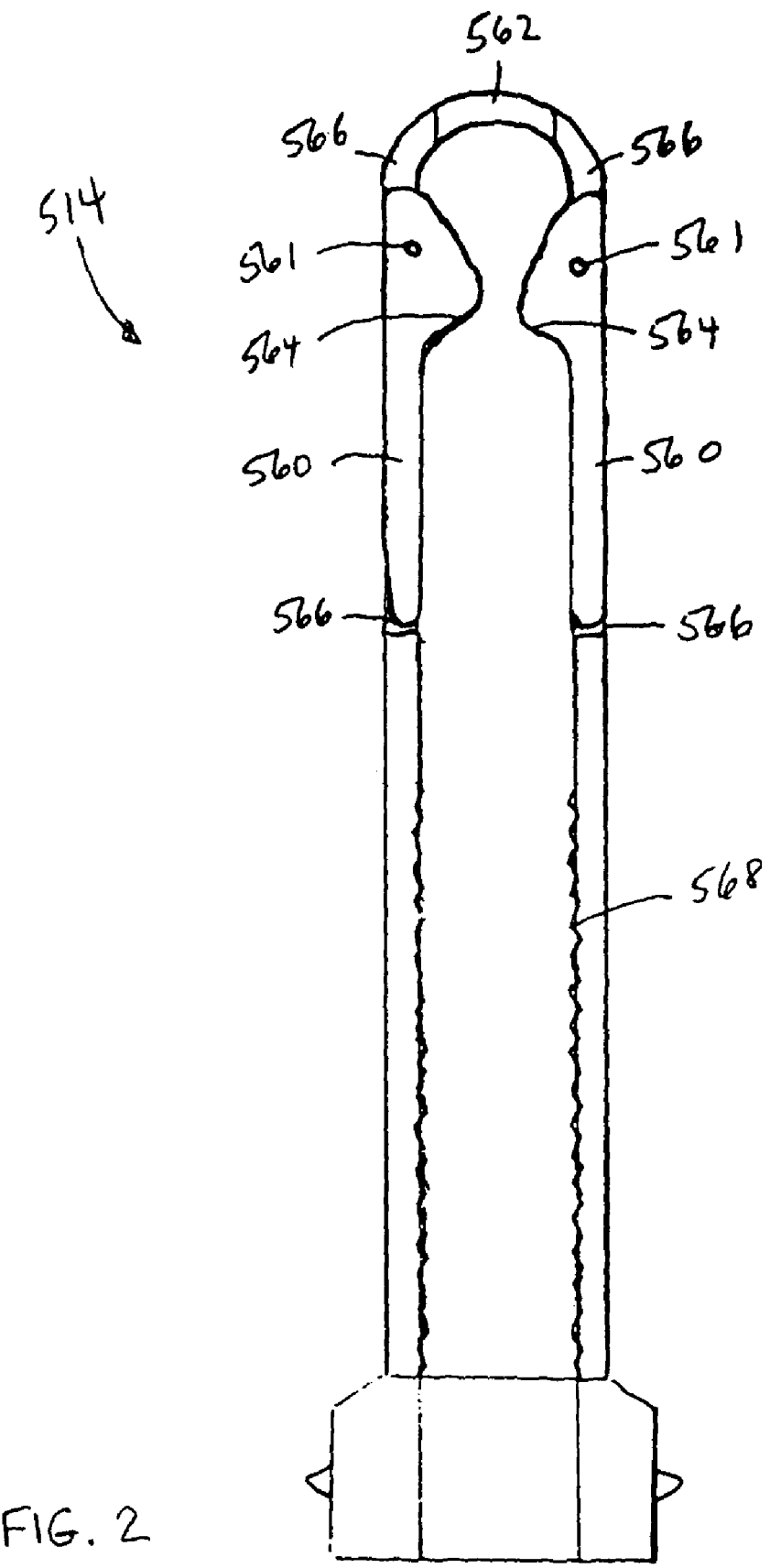
FIG. 2 is a schematic section view of a deployable post for the embodiment of FIG. 1, shown in a non-deployed configuration.

Turning now to FIG. 1, an embodiment of a proximal humeral fracture fixation system 510 according to the invention is shown. The system 510 includes a humeral plate 512 with one or more post holes 536 in a head portion 534 thereof and screw holes 532 along a shaft portion 530 thereof. A tubular post 514 is provided for each post hole 536. Referring to FIGS. 1 and 2, the post 514 includes a pair of arms 560 which are rotatably coupled about axes 561 adjacent the distal end 562 of the post 514. Embodiments with three or more arms may also be provided. Each arm 560 includes a cam follower surface 564 generally adjacent its pivot axis 561. When the cam follower surface 564 is subject to force in the distal and lateral directions, the arms 560 are moved into a radially open configuration, as shown in FIG. 1 and discussed further below. The post 514 includes windows 566 such that, when the arms 560 are in a closed position (FIG. 2), the arms 560 may lie flush with the remainder of the post. Referring to FIG. 2, the post also includes an internal thread 568.

Figure 3:
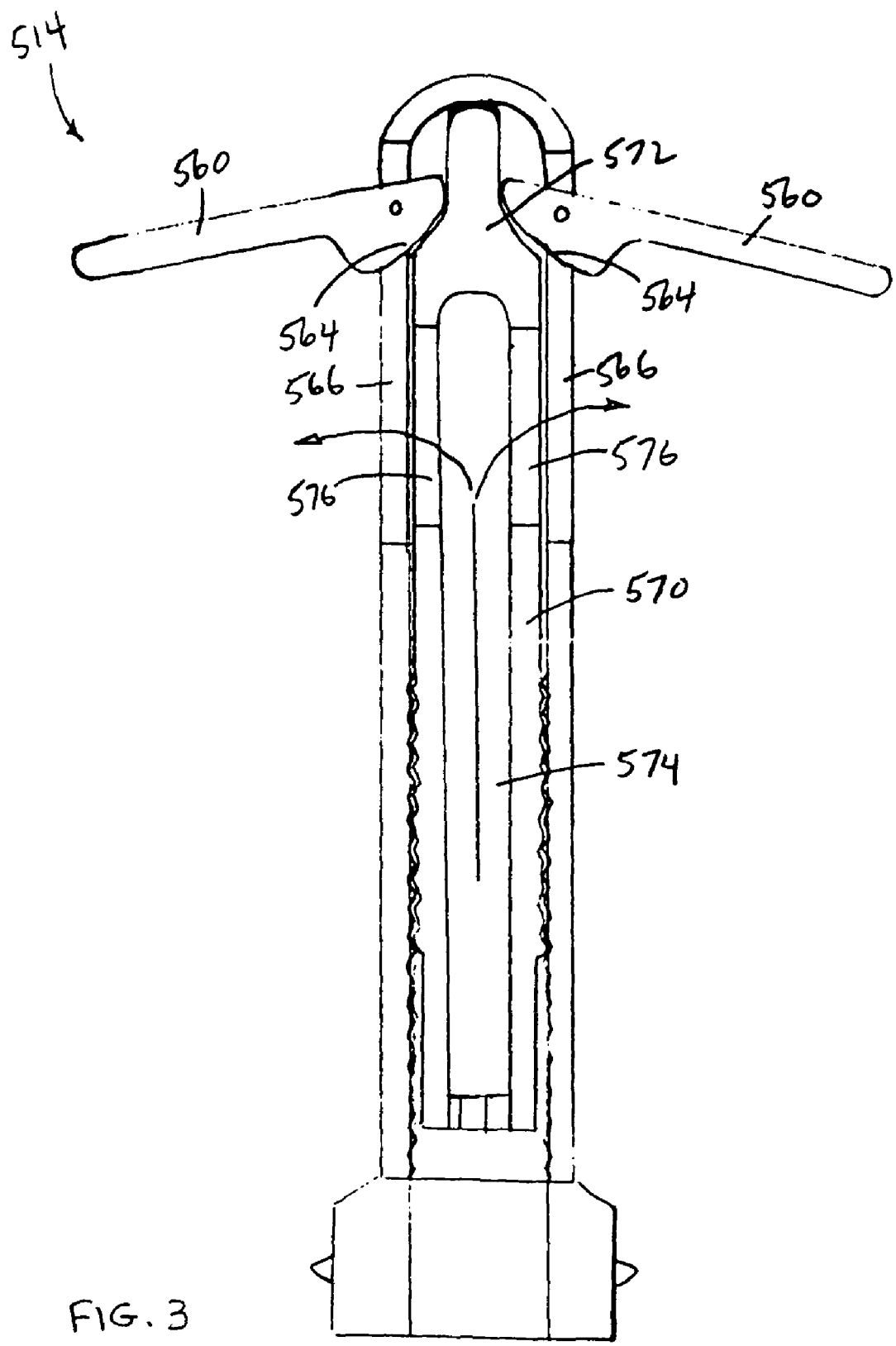
FIG. 3 is a schematic section view of a deployable post for the embodiment of FIG. 1, shown in a deployed configuration.

Referring to FIG. 3, a set screw 570 is provided which engages the internal thread 568 and includes a distal end provided with a cam 572 which operates to contact the cam follower surfaces 564 and move the arms 560 radially outward into the open configuration. In the open configuration, the arms 560 may each extend substantially 90° relative to the post 514; i.e., generally parallel to the articular surface and preferably in the anterior-posterior plane. However, it is even more preferable that the angle between each arm 560 and the post 514 be acute, and preferably approximately 60° to 89°, so that the arms better approximate the contour of the articular surface of the humeral head. While the arms 560 are surrounded by bone, the bone is often spongy or brittle osteoporotic bone which permits movement of the arms therethrough. The arms 560 shown are relatively broad providing significant stability to the fracture and support to the articular bone surface once moved into the open configuration. However, in order to facilitate movement through the bone, the arms may be relatively thinner than shown. Furthermore, the set screw may optionally include a bore 574 and distal openings 576 aligned with the windows 566 through which a preferably biodegradable bone cement or other preferably quick-setting filler material may be injected into the space created by the opening of the arms 560 (as shown by the arrows) to provide additional stability to the reduced fracture.

Figure 4:
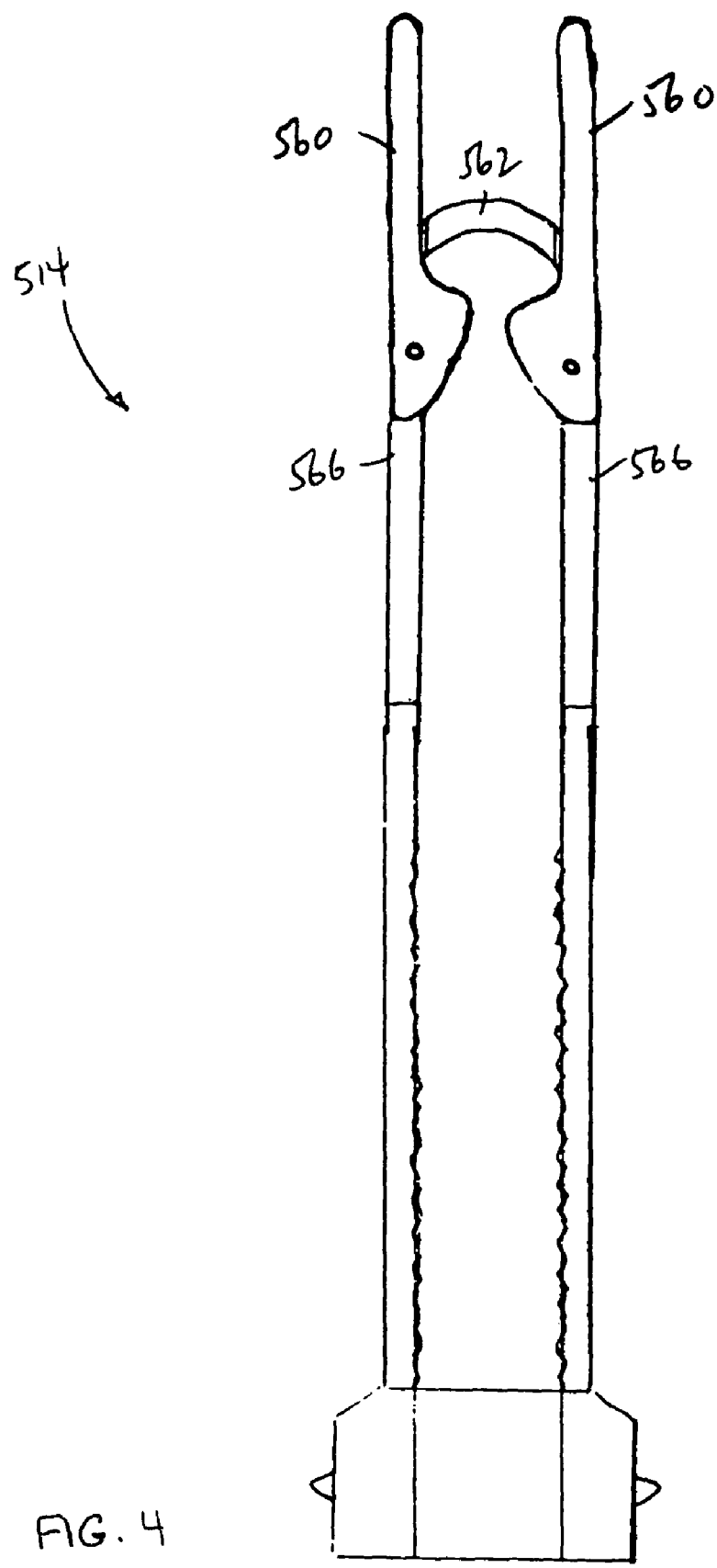
FIG. 4 is a schematic section view of a deployable post for the embodiment of FIG. 1, shown in a released configuration.

Referring to FIG. 4, if it is necessary or desirable to remove the post 514 and its arms 560 from the bone after implantation, the set screw 570 is unthreaded and removed from the post 514, and the post is then pulled from the bone. With the set screw 570 removed, the arms 560 are able to rotate upwards toward the upper end of the window 566 and stop against the distal end 562 of the post 514 as the post is withdrawn.

Figure 8:
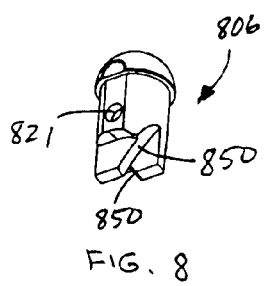
FIG. 8 is a perspective view of a distal tip of the deployable post of FIG. 5.

Turning now to FIGS. 5 through 11, another deployable post 714 is shown. The outer section of the post 714 includes a proximal tubular back end 802 (FIGS. 6A and 6B), a central tube 804 (FIG. 7) and a distal tip 806 (FIG. 8). Referring to FIGS. 6A and 6B, the back end 802 includes a head 807 with reference structure, e.g., scalloped notches 808, for rotationally orienting the post 802 relative to the humeral plate (as described in more detail below) and steps down to intermediate and smaller diameter portions 809, 810. The smaller diameter portion 810 defines two diametrically opposed wells 812. The distal end of the back end 802 further includes an internal thread 817. The tube 804 seats over the smaller diameter portion 810 and includes two distally directed wings 814 which engage in the wells 812 and lock the tube 804 on the back end 802 in a flush engagement with the intermediate diameter portion 809 of the back end 802. The tube 804 includes a pair of windows 852. The tip 806, also described further below, extends into the distal end of the tube 804 and is fixed in position on the tube with a pin 818 extending through holes 819, 821 in the tube 804 and tip 806, respectively.

Figure 5:
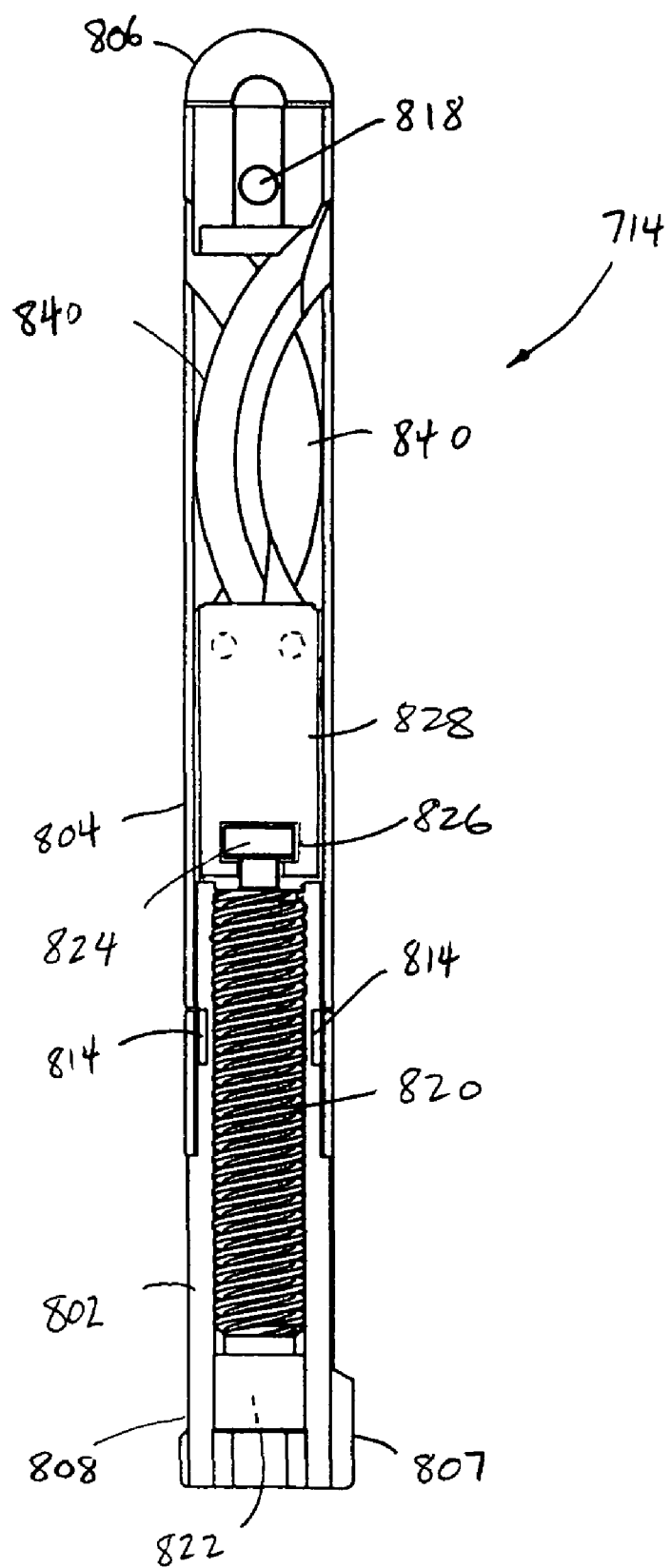
FIG. 5 is a longitudinal section view of another embodiment of a deployable post, with the deployable anchors in a non-deployed configuration.
Figure 6A:
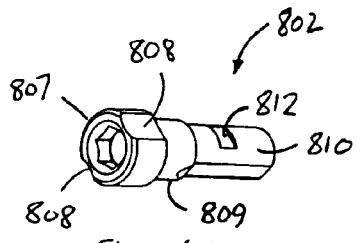
FIG. 6A is a perspective view of a back end of the deployable post of FIG. 5.
Figure 6B:
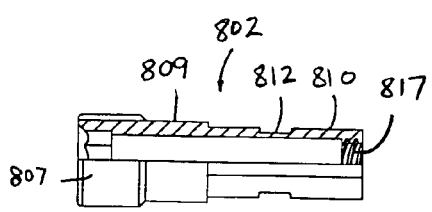
FIG. 6B is a longitudinal section view of the back end of the deployable post of FIG. 5.
Figure 7:
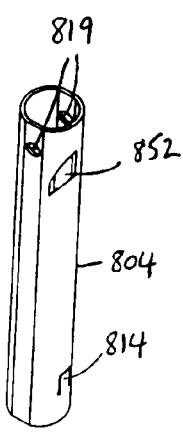
FIG. 7 is a perspective view of a central tube of the deployable post of FIG. 5.
Figure 9:
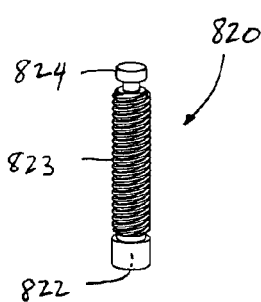
FIG. 9 is a perspective view of a lead screw of the deployable post of FIG. 5.
Figure 10:
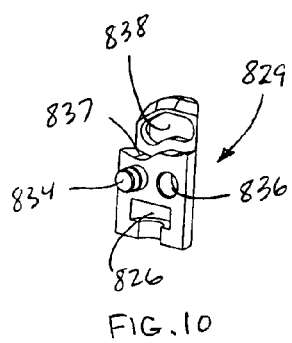
FIG. 10 is a perspective view of a coupler of the deployable post of FIG. 5.

Referring to FIGS. 5 and 9, a lead screw 820 is provided in the back end 802 of the post 714. The lead screw 820 includes a proximal engagement socket 822, e.g., square or hex socket, facilitating rotation of the lead screw 820 relative to the back end 802 by a tool, a threaded central portion 823 which engages the internal thread 817 of the back end 802, and a distal stepped head portion 824. The head portion 824 is captured by, and rotatable relative to, a nest 826 of a coupler 828. Coupler 828 is defined by a two hermaphroditic elements 829 (FIG. 10), which each include a post 834 and socket 836 which mate with corresponding parts on a like element. Each hermaphroditic element 829 also defines a track 837 and/or slot 838 into which a portion of an anchor 840 is movably coupled, as discussed below.

Figure 11:
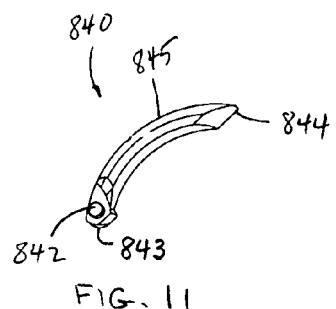
FIG. 11 is a perspective view of a bone anchor of the deployable post of FIG. 5.

Referring to FIG. 11, the bone anchors 840 include proximal axles 842 sized to travel within the slots 838 of the coupler 828 and have a back end 843 designed to ride along the track 837 of the coupler. The anchors 840 are curved along an arc, and each has a relatively sharp bone piercing end 844. The anchors are preferably made of metal, but may be made of ceramic or a stiff bioabsorbable material. Referring to FIGS. 8 and 11, the tip 806 defines two anchor guides 850 which each have a curvature corresponding to that of the convex side 845 of the anchors 840. The tube 804 defines two windows 852, corresponding to the cross-sectional shape of the anchors 840, through which the anchors 840 can be advanced out of the post 714.

Figure 13:
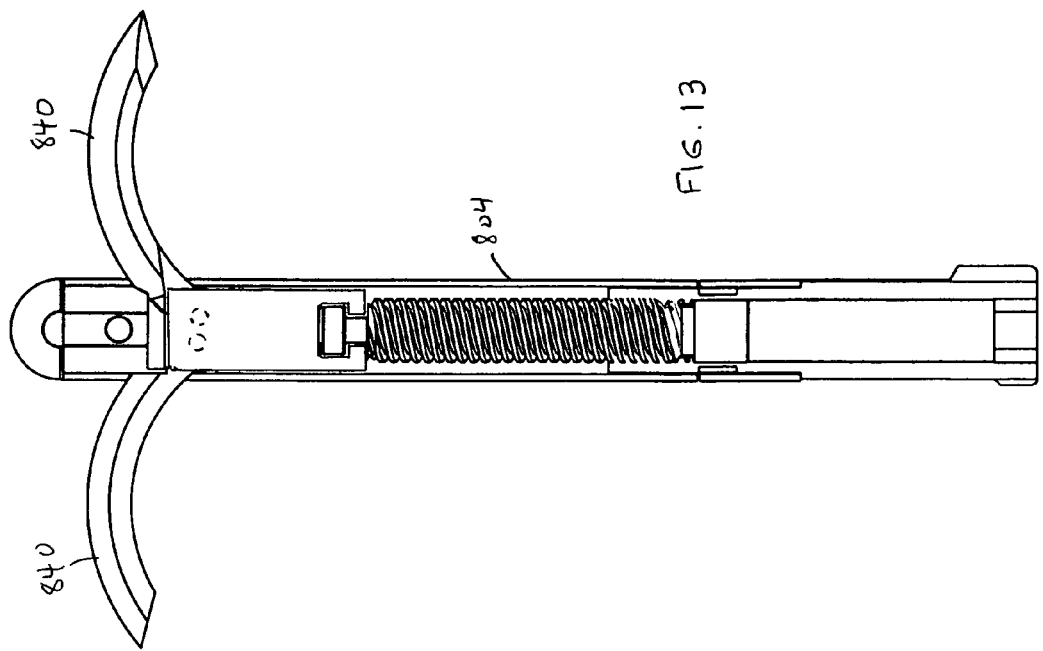
FIG. 13 is a longitudinal section view of the deployable post of FIG. 5, shown in a fully deployed configuration.
Figure 12:
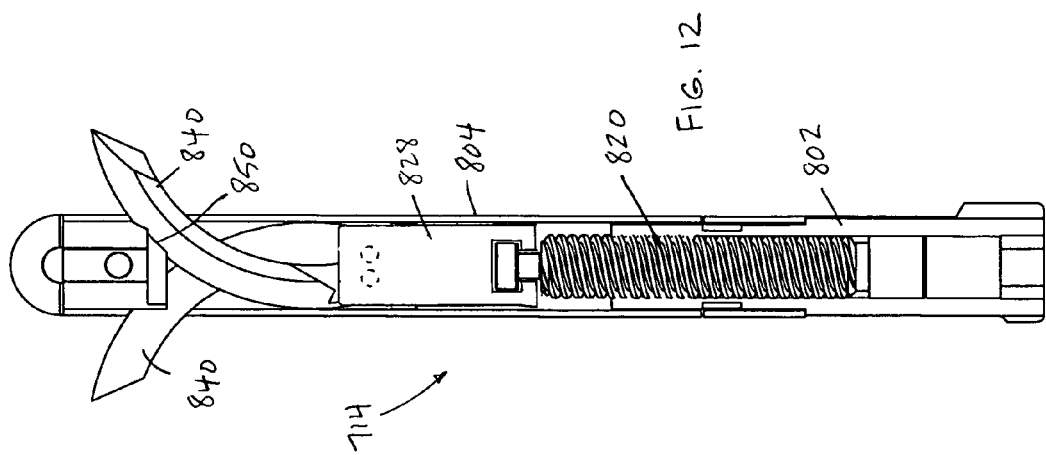
FIG. 12 is a longitudinal section view of the deployable post of FIG. 5, shown in a partially deployed configuration.

Referring to FIGS. 12 and 13, the lead screw 820 is rotationally advanced through the back end 802 to thereby cause advancement of the coupler 828 through the tube 804. As the coupler 804 advances, the anchors 840 are pushed forward, contact the guides 850 and are deflected out of the windows 852 (FIG. 7) in an outward direction, i.e., generally transverse to the axis of the post 714. In accord with one aspect of the invention, as the anchors 840 move forward and rotate about axles 842, their axes of rotation within the tube 804 changes, particularly relative to the initial orientation shown in FIG. 5 (as indicated by the broken circular marks on the coupler). This is accommodated by the ability of the axles 842 to move laterally within the slots 838 of the coupler 828. Referring to FIG. 13, when fully deployed, the anchors 840 preferably project outwardly between 2 and 3.5 times the diameter of the tube 804. In a preferred embodiment, the tube 804 has a diameter of 4 mm, and the anchors 840 each project approximately 10 mm.

Figure 14:
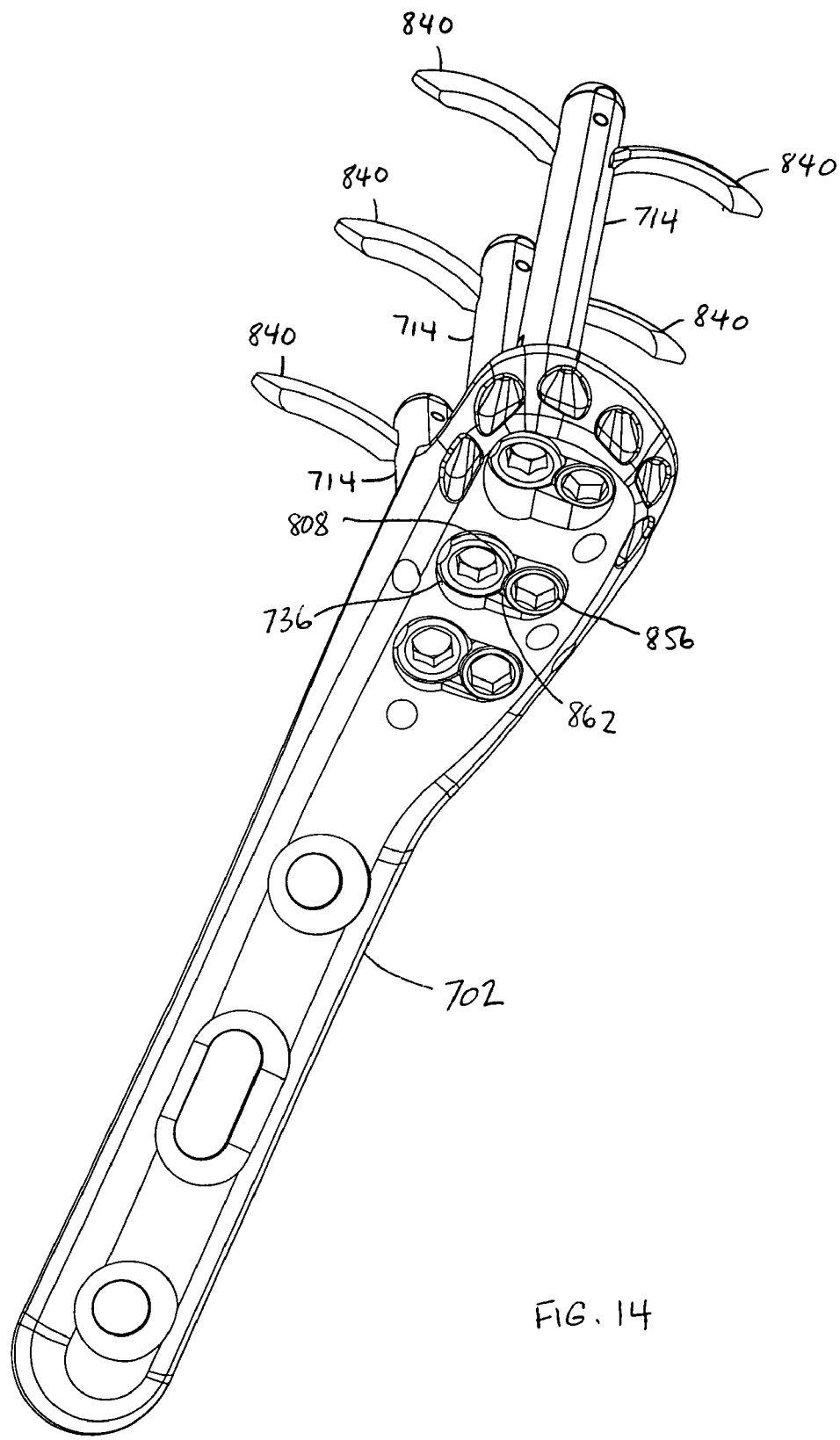
FIG. 14 is a perspective view of another system of the invention shown with deployable posts in the configuration of FIG. 13.

Turning now to FIG. 14, a humeral plate 702 is shown with a plurality of the posts 714 coupled thereto and with anchors 840 deployed. The posts 714 can be locked to the plate 702 in any suitable manner. However, it is preferable that the posts 714 be locked relative to the plate 702 so that the orientation of the deployed anchors 840 be predetermined, e.g., generally parallel to each other as shown. Moreover, it is preferable that each post 714 be locked relative to the plate 712 without a threaded coupling therebetween, as it is difficult to machine a threaded coupling in which (i) the components are both fixedly and rigidly coupled together, and (ii) in which the rotational orientation of the post can be predetermined with certainty upon locking. Notwithstanding the above, it is certainly possible and within the scope of the invention to machine a threaded coupling between the post and the plate with the entry and termination points arranged and with the required tolerances to obtain the same results; i.e., predetermined rotational orientation upon fully seating the post in the plate.

In accord with a preferred aspect of the present embodiment, the lock between a post 714 and its respective post hole 736 preferably occurs within less than one complete rotation of the post 714 relative to the post hole 736, and more preferably within 0° to 90° rotation.

Figure 15:
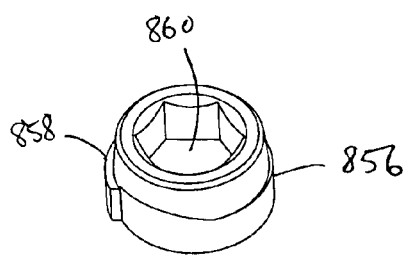
FIG. 15 is a perspective view of a cam for the system of FIG. 14.

One method of locking the posts is to use a cam to lock each post within the plate. Referring to FIG. 15, a preferred cam 856 is generally cylindrical, but has an outer wall 858 that spirally increases in radius about approximately 270° of the circumference of the cam. The cam 856 also includes a lower pin (not shown) about which the cam rotates, and an upper hex slot 860 for a driver.

Figure 17:
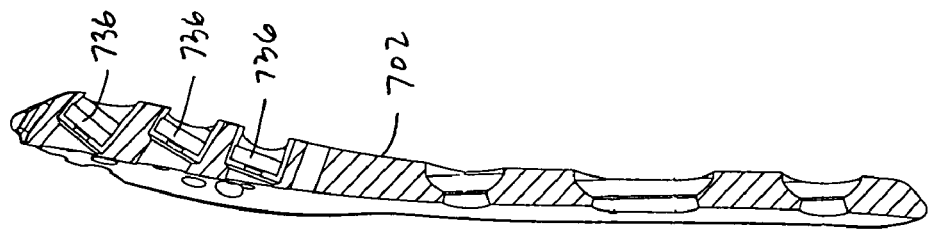
FIG. 17 is a longitudinal section view along line 17-17 in FIG. 16.
Figure 16:
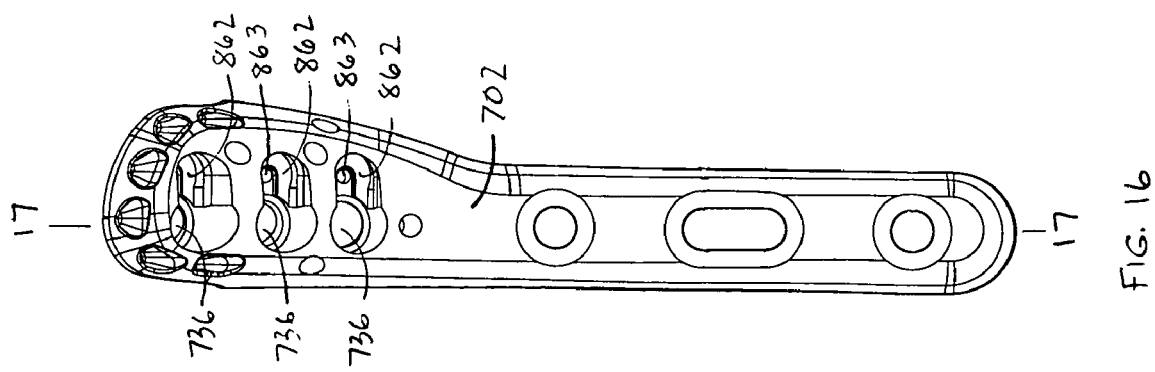
FIG. 16 is a plan view of the plate of the system of FIG. 14.

Referring to FIGS. 14, 16 and 17, for each post 714, the plate 702 includes a post hole 736 and an adjacent recessed cam slot 862 with a centering hole 863 which receives the centering pin. As a result of the shapes of the cam 856 and the cam slot 862, once the cam is received in the cam slot, the cam is essentially trapped therein. Before inserting the post 714 into the post hole 736, the cam 856 is rotated so that its smallest radius is positioned toward the post hole. The post 714 is received through the post hole 736, oriented so that a scalloped notch 808 at the back end 802 of the post fits about the outside of the cam 856, and pushed fully into the post hole. The cam 856 is then rotated with a driver to provide contact between a larger radiused portion of the cam and the post to provide sufficient contact therebetween to effectively lock the post 714 to the plate 702.

Figure 18:
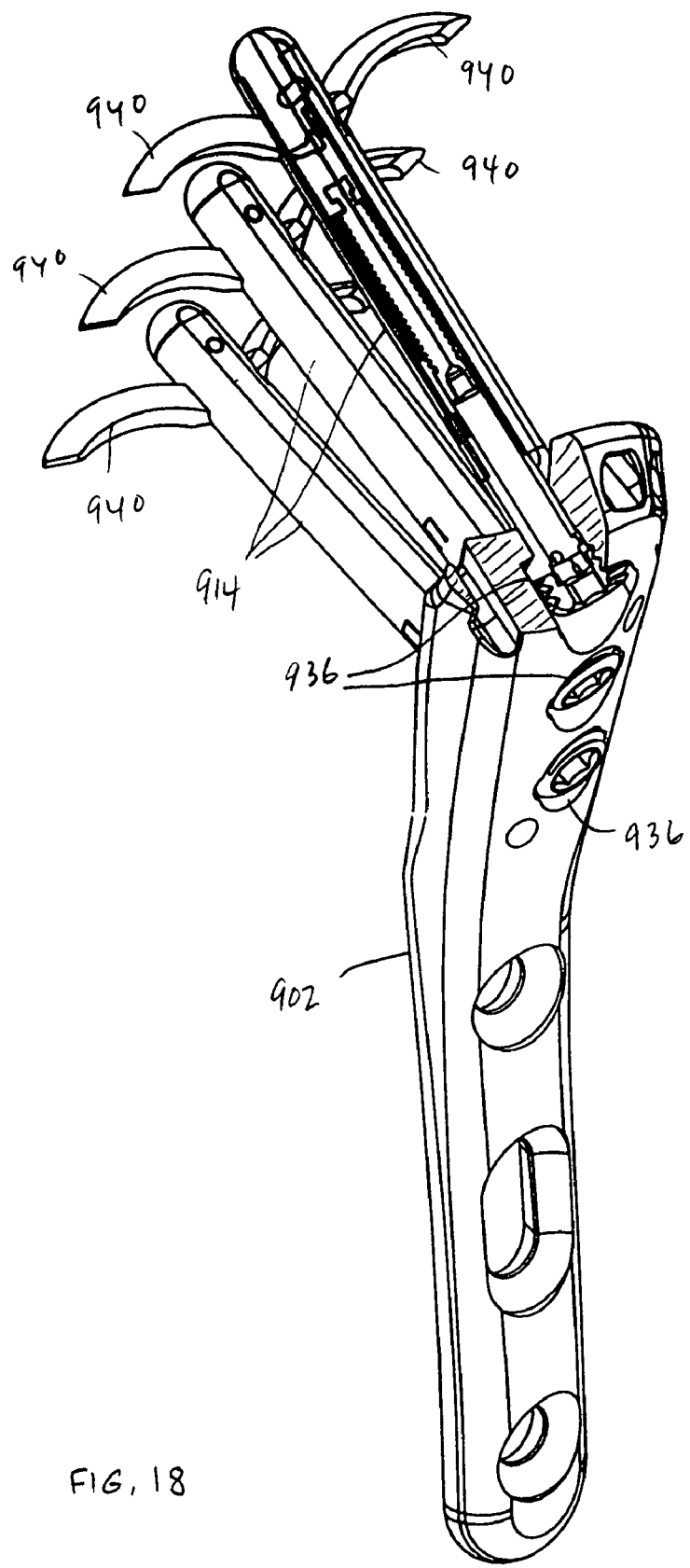
FIG. 18 is a perspective view of another system of the invention shown with the posts in a deployed configuration.
Figure 19:
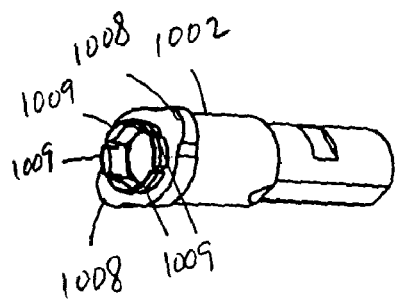
FIG. 19 is a perspective view of a back end of the deployable posts used in the system shown in FIG. 18.
Figure 20:
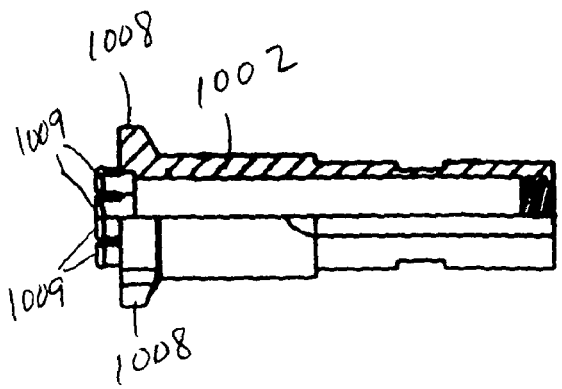
FIG. 20 is a longitudinal section view of the back end of the FIG. 19.
Figure 21:
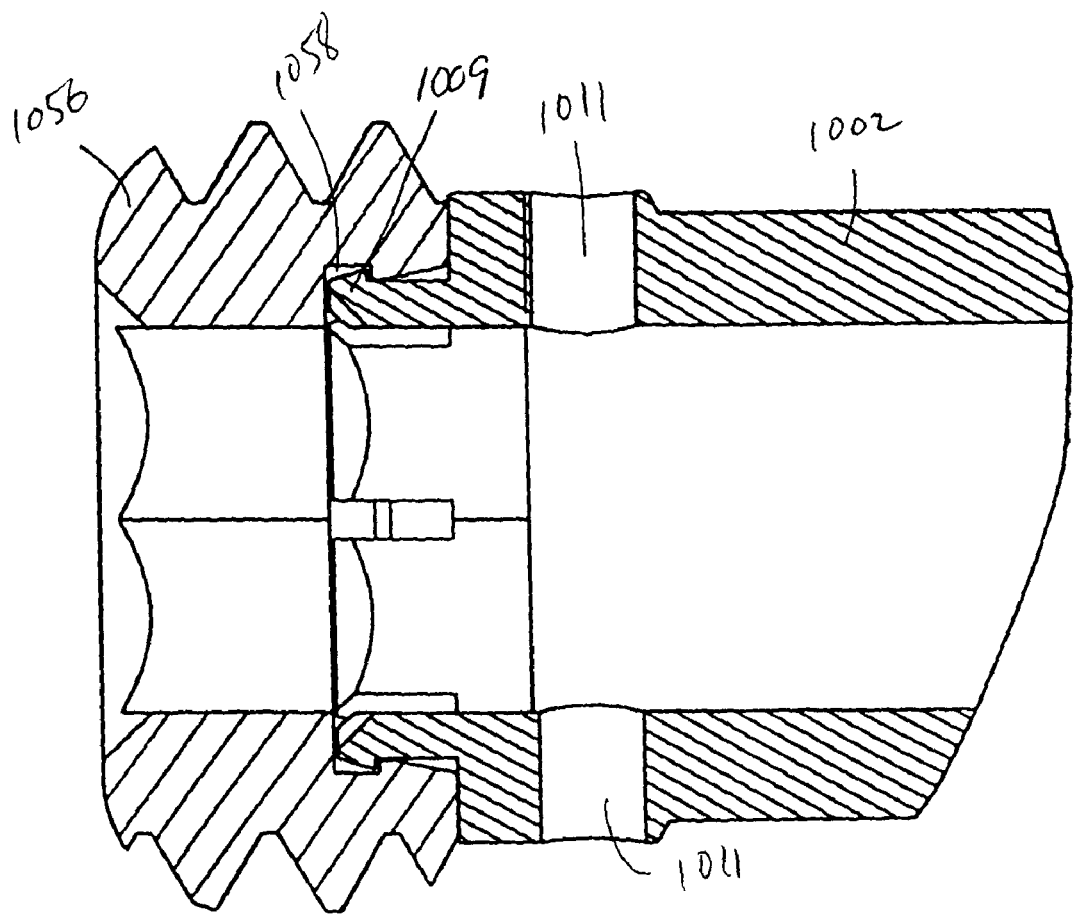
FIG. 21 is an enlarged broken section view of the back end and a set screw of the system shown in FIG. 18.

Turning now to FIGS. 18 through 20, another embodiment of a system for rotationally and axially locking the posts relative to the plate is shown. In accord with such system, the posts 914 are substantially as described above with respect to post 714. In contrast to post 714 (FIG. 5), the back end 1002 of the post 914 includes ears 1008 and a circular arrangement of resilient, radially outwardly directed catches 1009. In addition, referring to FIG. 21, the back end 1002 of post 914 includes a diametric bore 1011 to facilitate removal of an implanted post, if necessary, as described in more detail below. Still referring to FIG. 21, the system includes a set screw 1056 which locks the post 914 relative to the plate 902, as also described below. The set screw 1056 includes a recess 1058 in which the catches 1009 engage, but which also allows the set screw 1056 to be rotatable relative to the catches.

Figure 22:
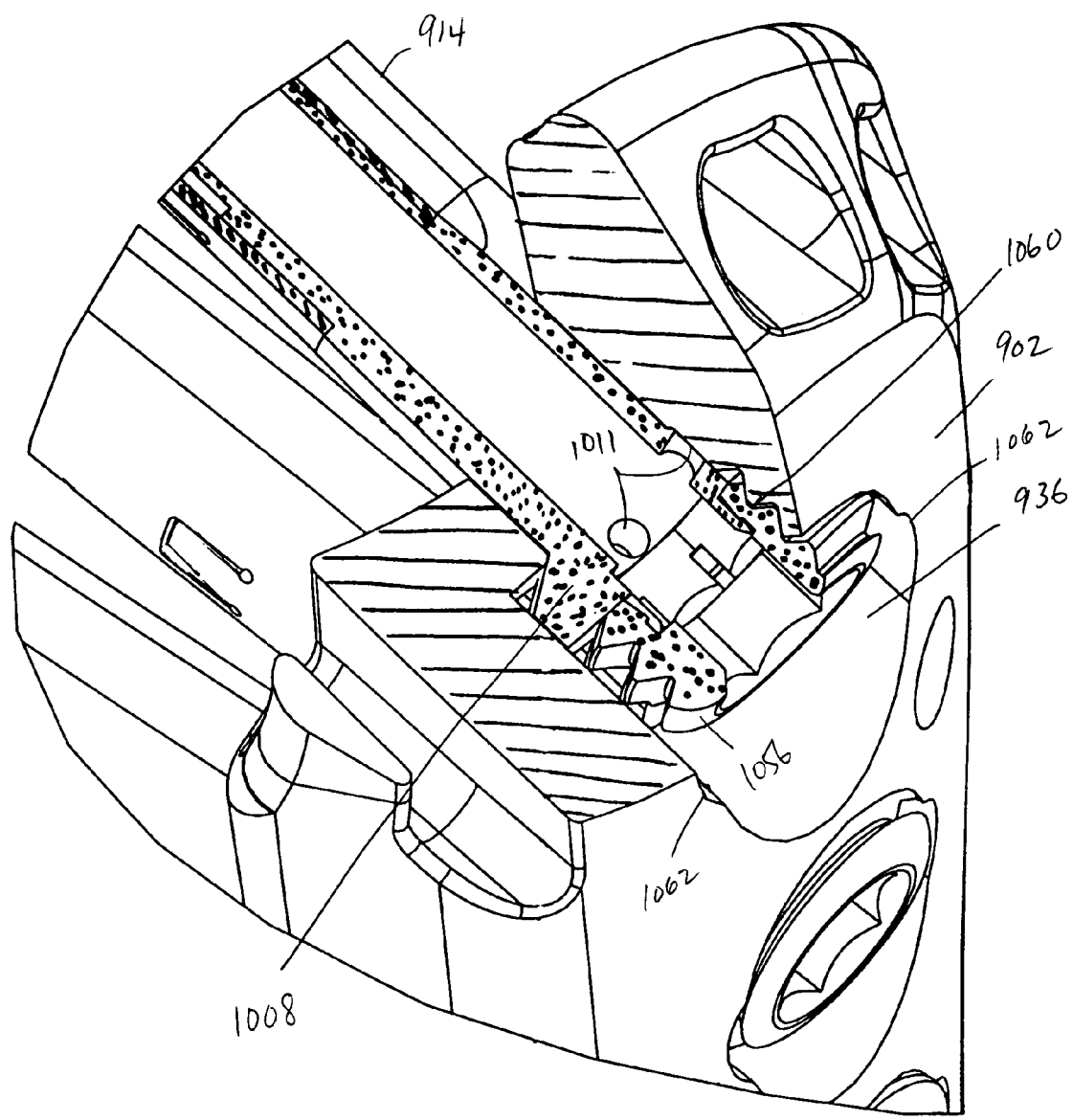
FIG. 22 is a broken partial section perspective view of the system shown in FIG. 18.

Referring now to FIG. 22, each post hole 936 of the plate 902 is stepped in diameter, includes threads 1060 within an upper larger diameter portion, and two diametric ear portions 1062. The post 914 is inserted through the post hole 936 so that the ears 1008 align with the ear portions 1062. This ensures proper alignment of the anchors when they are later extended (FIG. 18). Then, the set screw 1056 is rotated in engagement with the threads 1060 and rotated until the post 914 is rigidly locked in place.

If necessary, to remove the post 914, the set screw 1056 is rotated into disengagement. In doing so, the set screw may release from the post. Should this occur, a tool (not shown) may be inserted into the diametric bore 1011 and pulled to withdraw the post from the bone and hole 936.

Figure 23:
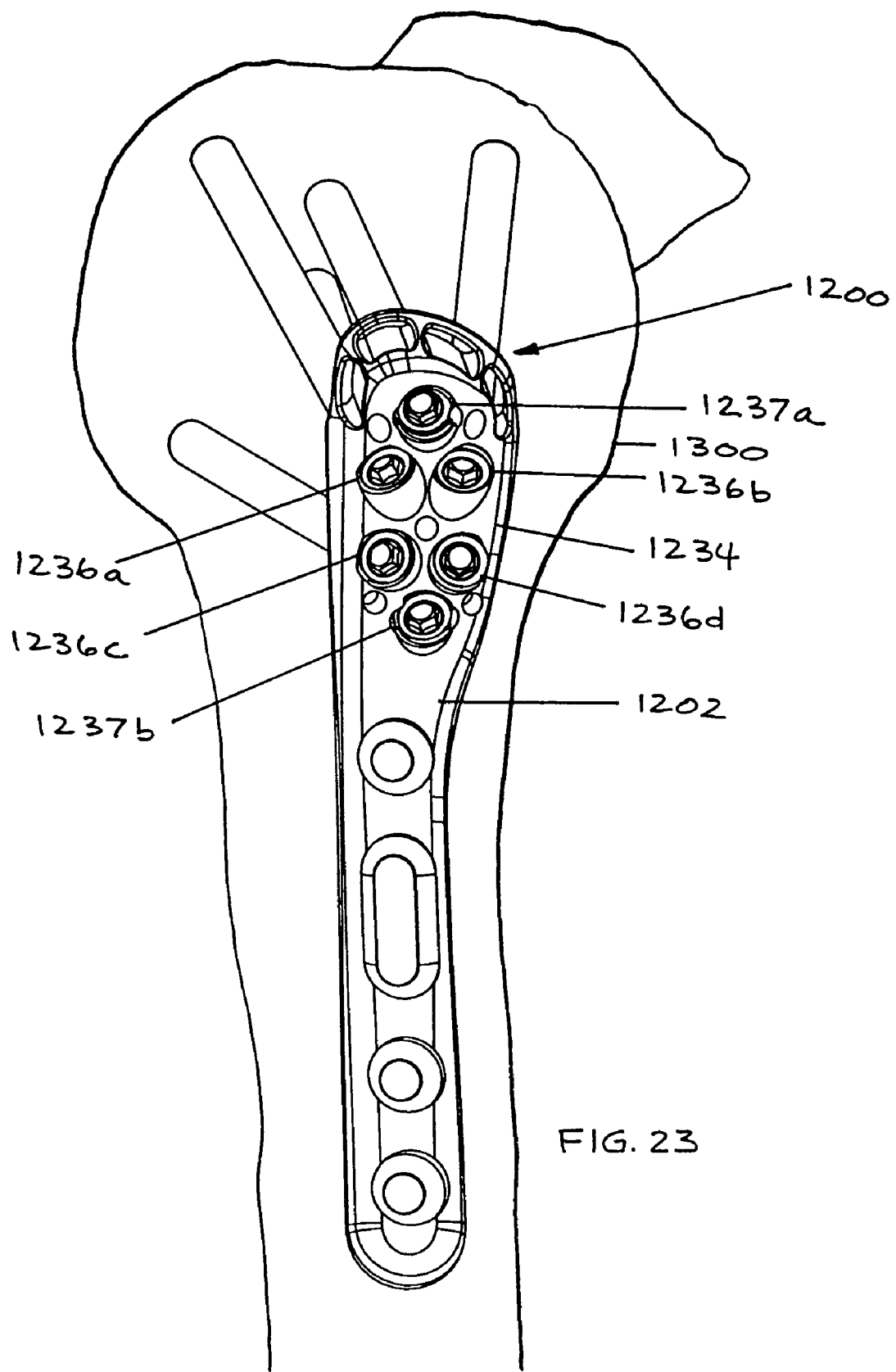
FIG. 23 is a lateral perspective view showing another embodiment of a proximal humeral fracture fixation system of the invention in place on the bone.
Figure 24:
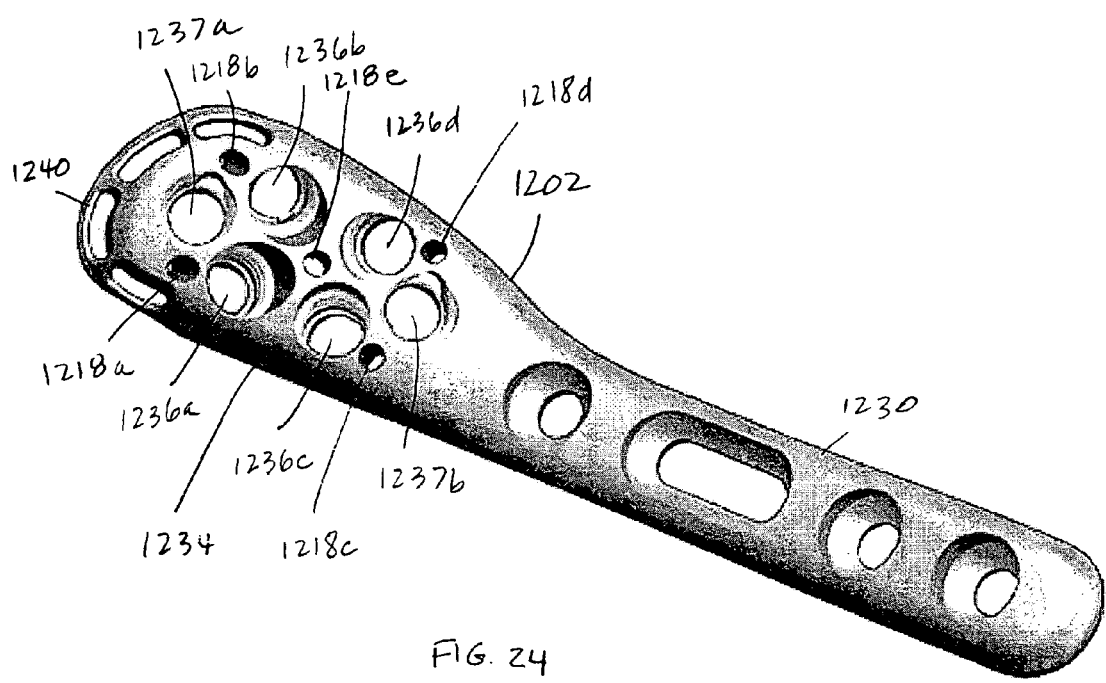
FIG. 24 is a perspective view of a plate of the system of FIG. 23.
Figure 25:
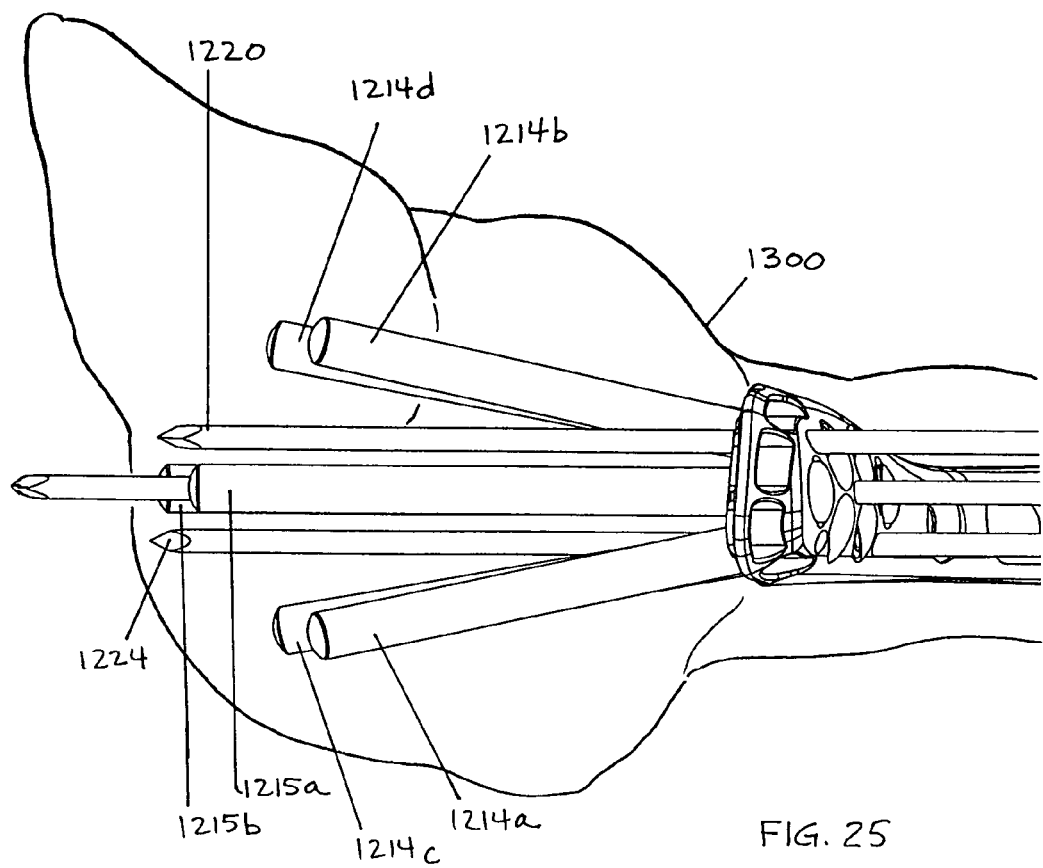
FIG. 25 is a top view of the fixation system of FIG. 23, shown implanted.
Figure 26:
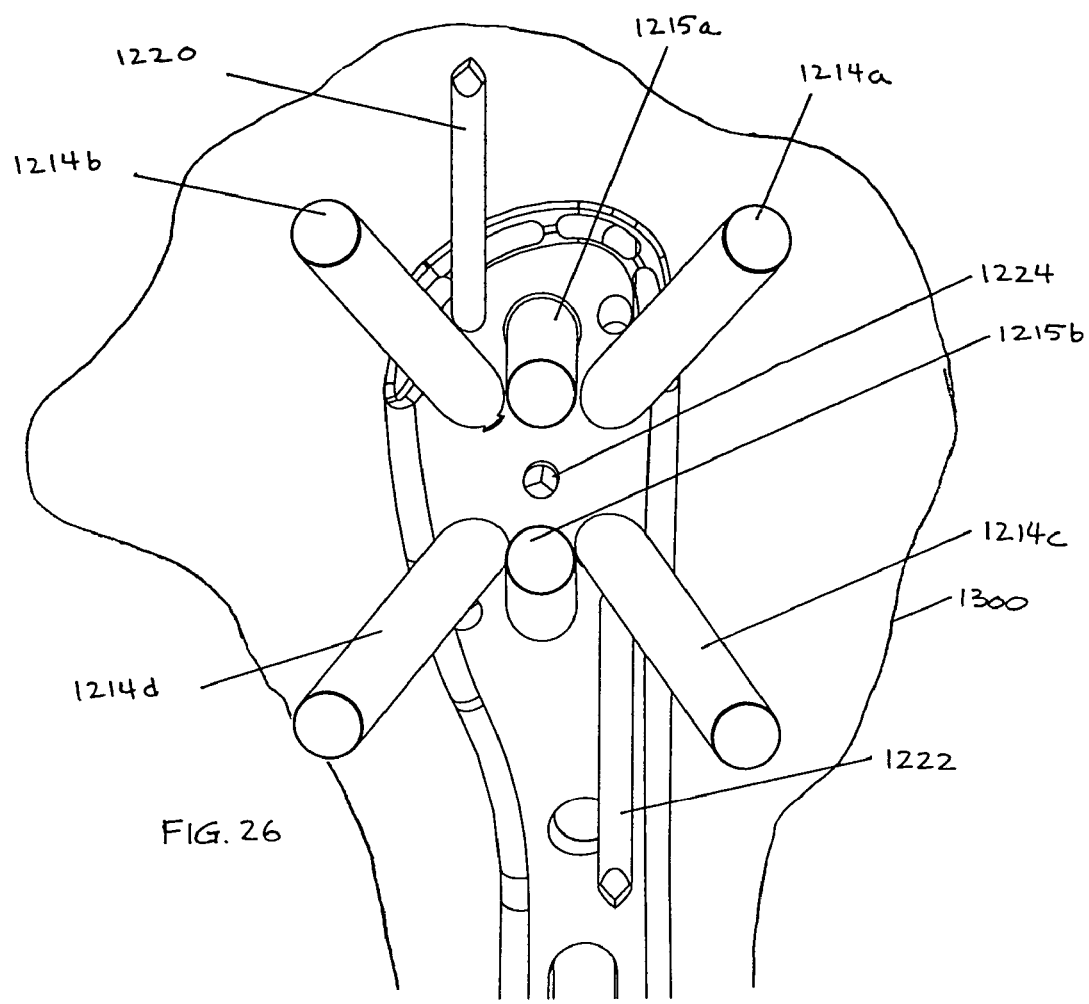
FIG. 26 is a medial view from within the bone of the fixation system of FIG. 23.

Turning now to FIGS. 23 through 28, another embodiment of a fixation system 1200 is shown attached to a humerus 1300. Referring to FIGS. 23 and 24, the system 1200 includes a plate 1202 having a head portion 1234 with six post holes, including central post holes 1236*a*, 1236*b*, 1236*c*, 1236*d* (collectively, 1236) designed to accept posts having a threaded head, and proximal and distal posts 1237*a*, 1237*b* (collectively, 1237) which are preferably substantially similarly to post holes 936 (FIG. 22) for receiving posts which may optionally have deployable anchors. That is, post holes 1237 preferably include a system which locks the angular orientation of the post. Such system is also adapted to receive conventional threaded-head posts (with or without out any deployable support means for supporting the subchondral bone of the articular surface), as shown in FIGS. 25 and 26. Further, where posts without any support means are used, the post holes do not require any system for angularly indexing or precisely fixing the posts. Referring still to FIGS. 25 and 26, the central post holes 1236*a*, 1236*b*, 1236*c*, 1236*d* define axes illustrated by the posts 1214*a*, 1214*b*, 1214*c*, 1214*d* therethrough which are angularly oblique from each other, causing the posts to diverge both laterally and longitudinally. The proximal and distal post holes 1237*a*, 1237*b* define axes which are preferably laterally aligned and angularly convergent, as illustrated by posts 1215*a*, 1215*b*.

Referring to FIG. 24, the head portion 1234 is also provided with five alignment holes 1218*a*, 1218*b*, 1218*c*, 1218*d*, 1218*e* (collectively, 1218), each sized to closely receive a K-wire (substantially smaller than a respective post for the post holes) along a fixed axis. Specifically, the axis of 1218*e* is directed toward the center of the articular surface of the humeral head. The alignment holes 1218 are angularly oriented within the head portion 1234 of the plate so as to present a path for K-wires which will outline various boundaries of the posts or identify a point of interest relative to the implanted posts. More particularly, as shown in FIGS. 24 through 26, K-wires 1220, 1222 positioned in holes 1218*b*, 1218*c* define the upper and lower bounds of posts 1214*a*, 1214*b*, 1214*c*, 1214*d*, while K-wire 1224 positioned in hole 1218*e* is directed to the center of the articular surface and defines a central location towards which the axes of the proximal and distal post holes 1215*a*, 1215*b* converge.

Figure 27:
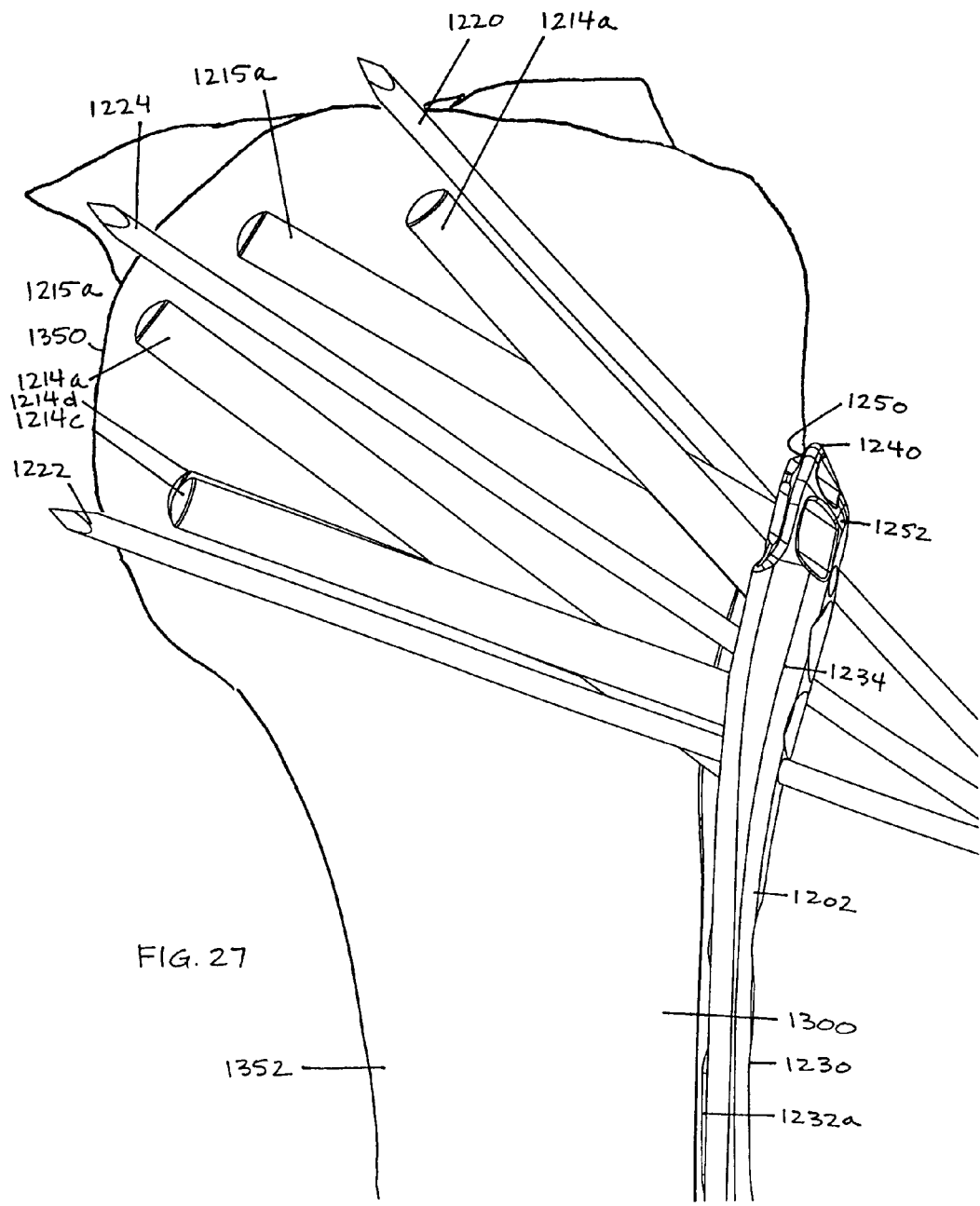
FIG. 27 is another view of the implanted fixation system of FIG. 23.

As shown best in FIGS. 24 and 27, a narrow suture rail 1240 extends about the proximal portion of the head portion 1234. The suture rail 1240 is elevated relative to the lower surface 1250 of the head portion to facilitate entry of a suture needle through the rail and recessed relative to the upper surface 1252 to present a relatively low unobtrusive profile.

Figure 28:
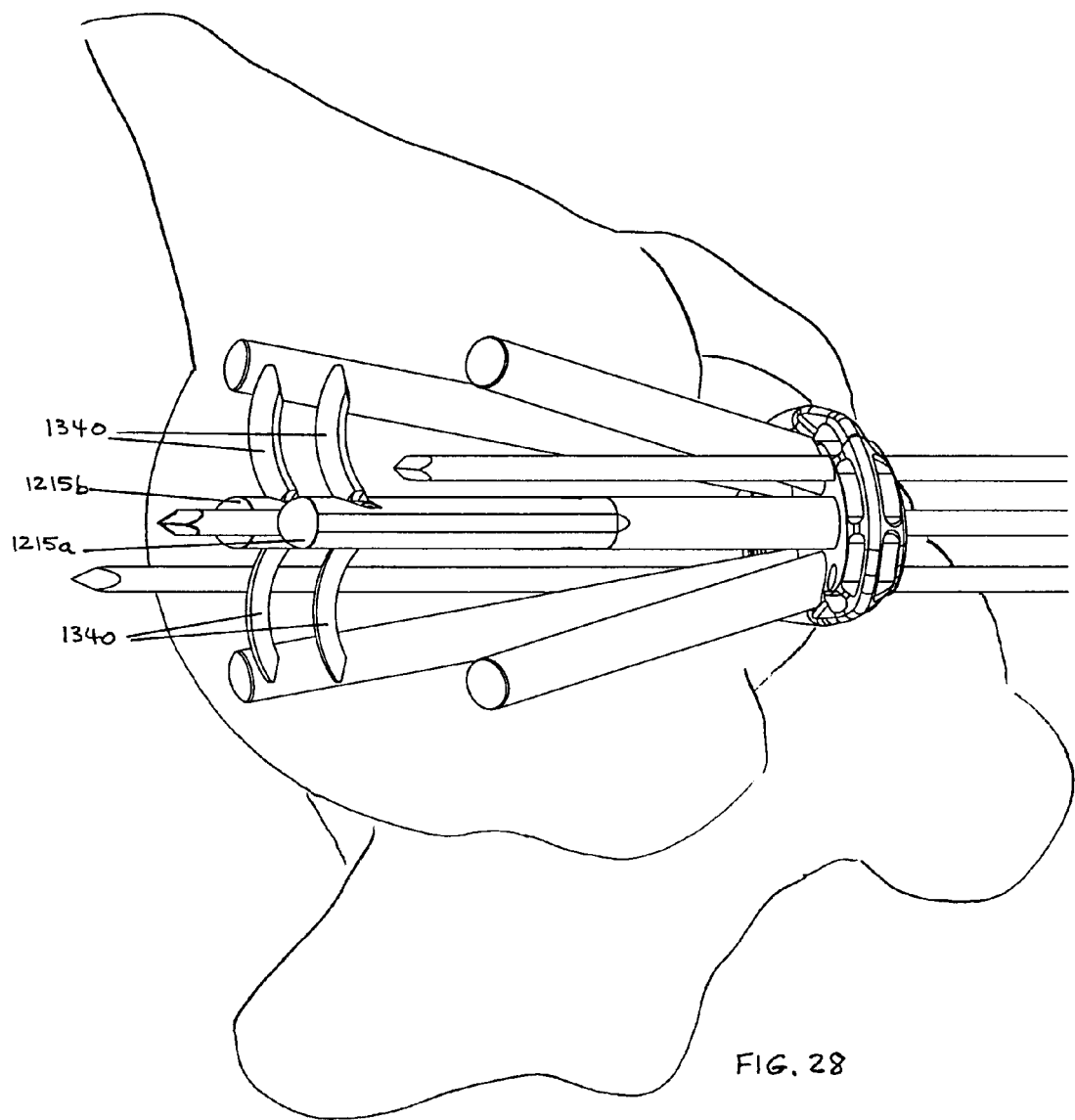
FIG. 28 is a view similar to FIG. 25 showing the system with deployed anchors.
Figure 29:
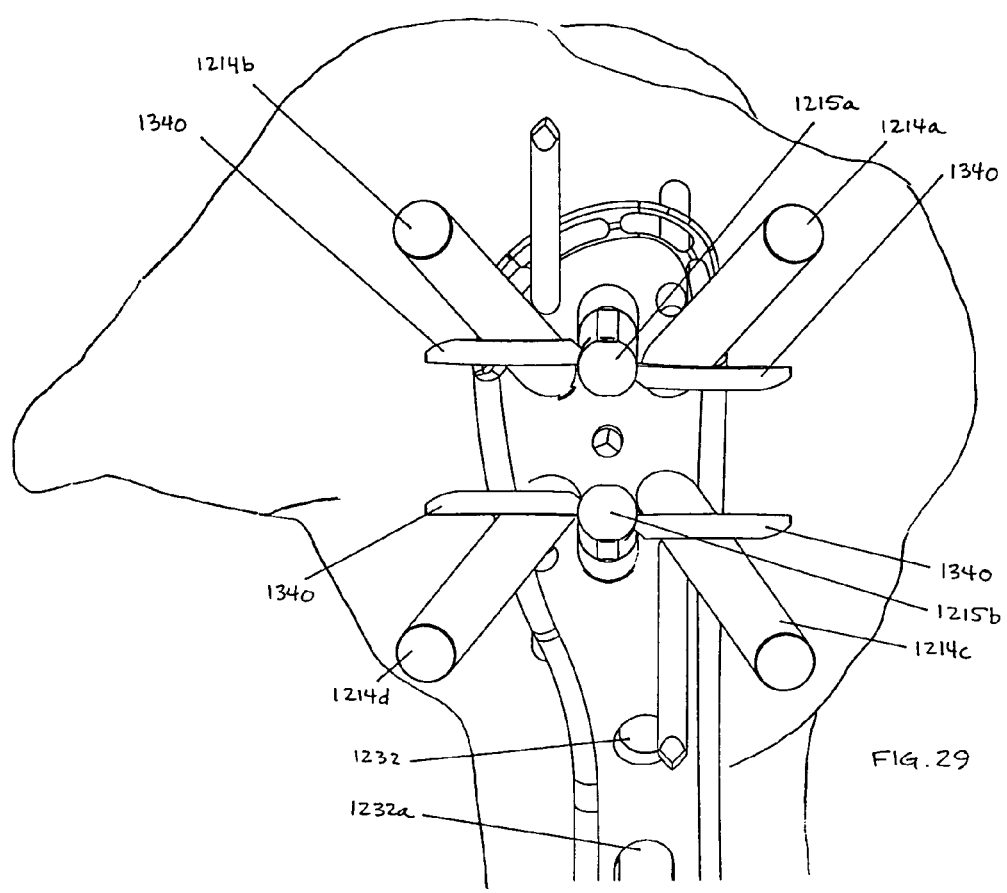
FIG. 29 is a view similar to FIG. 26 showing the system with deployed anchors.

Referring to FIGS. 27 through 29, in use, by way of a delto-pectoral approach, the fracture is exposed and debrided. Traction and direct manipulation are used to reduce the fracture, and the anatomical relationship between the articular surface of the subchondral bone 1350 and the humeral shaft 1352 is restored in both its angular alignment and retroversion. The position for the plate 1202 is then located on the humerus 1300, preferably immediately posterior to the intertubercle groove and approximately 1.5-2.0 cm below the insertion of the supraspinatus. The plate is then provisionally secured to the distal fragment using, e.g. 2.0 mm fixation K-wires inserted through the shaft of the plate or a cortical screw provisionally inserted through a non-locking oblong screw hole 1232*a*. The reduction is then locked by using K-wires 1220, 1222, 1224 inserted through the fixed angle K-wire holes on the head portion 1234 of the plate and into the proximal fragment(s). Multiple wires may be used to anticipate final post positions.

Axes of the alignment holes correspond to axes of adjacent post holes. Using preferably both anterior-posterior and axillary views, the K-wires 1220, 1222, 1224 are viewed fluoroscopically to provide an indication as to whether the posts will be properly oriented. If the placement is correct, the K-wires maintain the position of the plate over the fracture. The posts holes may then be drilled with confidence that their locations and orientations are proper. If placement is not optimal, the K-wires are removed and the surgeon can relocate the plate and/or can reorient the K-wires and drills again. Since each K-wire is of relatively small diameter, the bone is not significantly damaged by the drilling process and the surgeon is not committed to the initial drill location and/or orientation. The use of alignment holes and K-wires therethrough for an orthopedic plate is described in more detail in U.S. Ser. Nos. 10/689,797, filed Oct. 21, 2003, Ser. No. 10/664,371, filed Sep. 17, 2003, and Ser. No. 10/985,598, filed Nov. 10, 2004, which are hereby incorporated by reference herein in their entireties.

The shaft 1230 of the plate 1212 is then fixed to the humeral diaphysis 1352 by fully inserting the cortical screw through the oblong hole 1232*a*. Any K-wires that may have been used to secure the shaft are removed.

Using a drill guide (not shown), holes for the posts are drilled. Using a depth gauge (not shown), the depth of the drilled holes is determined. Appropriate length posts 1214*a*, 1214*b*, 1214*c*, 1214*d*, 1215*a*, 1215*b* are inserted using a driver. The distal end of the posts are preferably 4-6 mm below the articular surface of the subchondral bone 1350. Radiographic confirmation of the correct fracture reduction and post placement is then made.

Referring to FIGS. 28 and 29, where the posts 1215*a*, 1215*b* include deployable anchors, the surgeon deploys the anchors 1340 to provide support for the articular surface of the subchondral bone 1350. In practice, the K-wires 1220, 1222, 1224 in the head portion 1234 are preferably removed prior to anchor deployment.

Additional holes are also drilled for the remaining cortical screws that will be used to fix the distal part of the plate to the diaphysis 1352 of the humerus.

Next, if necessary, tuberosities are reduced and fixed to the suture rail 1240 of the plate using sutures or wires.

Final radiographic views are then taken and the surgical wound is closed using appropriate surgical technique.

Figure 30:
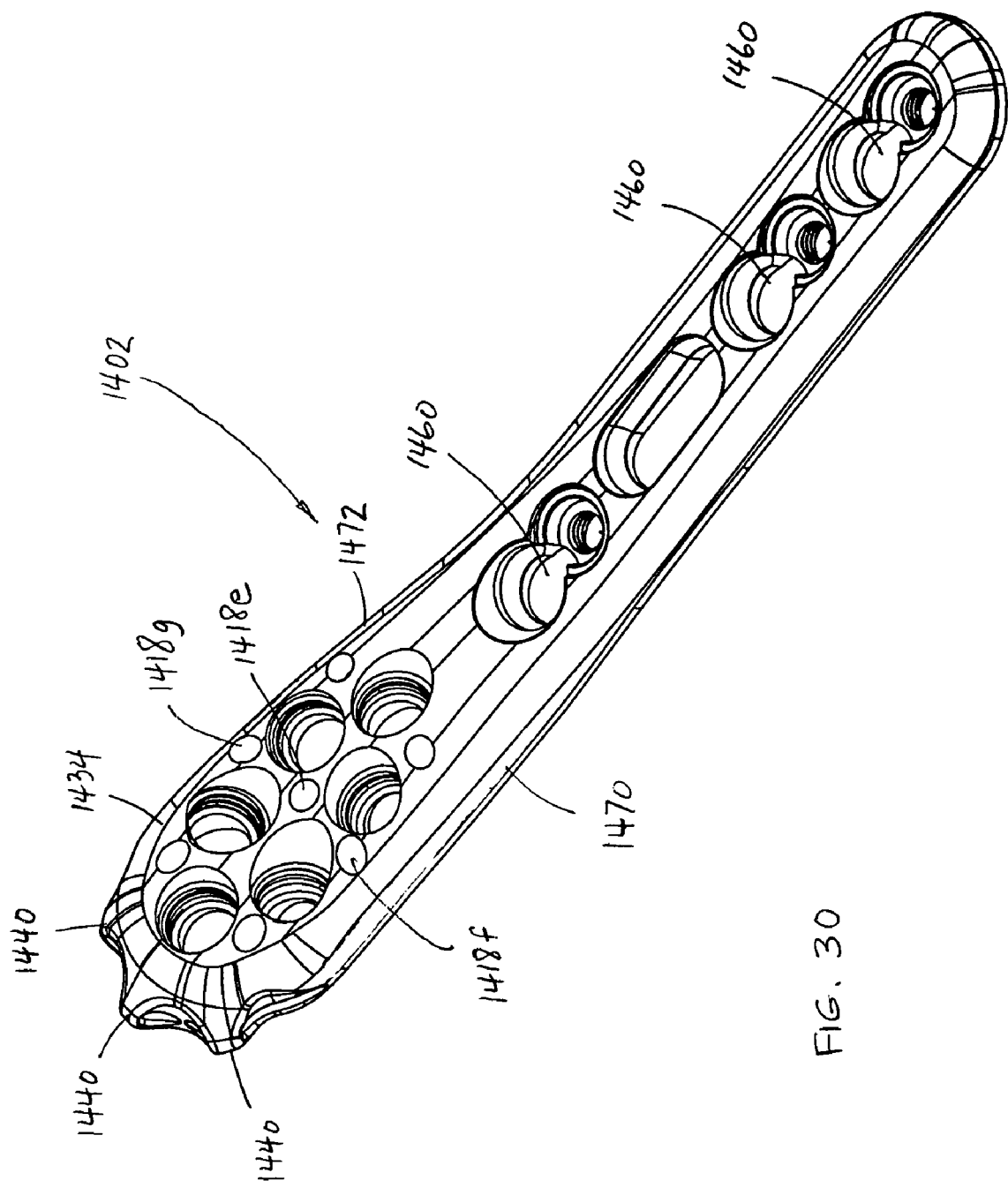
FIG. 30 is a perspective view showing another embodiment of a proximal humeral fracture fixation system of the invention.

Turning now to FIG. 30, another embodiment of a shoulder plate 1402 is shown. The plate 1402 is substantially similar to plate 1202 in features, but includes several significant structural distinctions. First, the proximal end of the head portion 1434 includes three discrete generally radially-arranged suture guides 1440 with lateral openings. The guides 1440 are spaced to permit needle access therethrough without obstruction from the adjacent guide(s). Second, additional K-wire openings 1418*f*, 1418*g* are provided anterior and posterior the central K-wire opening 1418*e* to permit the use of additional K-wires for fluoroscopic visualization of the arrangement of the posts within the bone prior to insertion of the posts. The additional openings 1418*f*, 1418*g* may be particularly useful where the surgical approach creates difficulty in the use of one or more of the other openings. Third, the bone screw holes 1460 are designed for use with specific cortical screws and set screws (not shown) which permits independent application of compression and locking of the cortical screw. Such screw holes, cortical screws and set screws, as well as other suitable screw systems which may be used in the fracture fixation systems described herein, are described in U.S. Ser. No. 11/040,779 filed simultaneously herewith, which is hereby incorporated by reference herein in its entirety.

It is noted that none of the shoulder plates are universal models, as the above described plate is adapted for placement on the left arm or the right arm, but not both. In accord therewith, each of the plates includes a substantially straight edge. When the head portion of the plate is positioned 1.5-2.0 cm below the insertion of the supraspinatus and the straight edge is aligned immediately posterior with the intertubercle groove, proper placement of the plate on the humerus is assured. For example, in FIG. 30, the straight edge is edge 1470, and opposite is a slightly curved edge 1472. The other shoulder plates described herein include corresponding straight and curved edges and when placed according to the above teaching provide the desired placement. Moreover, by locating the head portion of the plate at such a large distance relative to the insertion of the supraspinatus (which is in distinction from the significantly closer spacing in the prior art) the potential for interference between the head portion of the plate and the acromion when the arm is raised is minimized.

Figure 31:
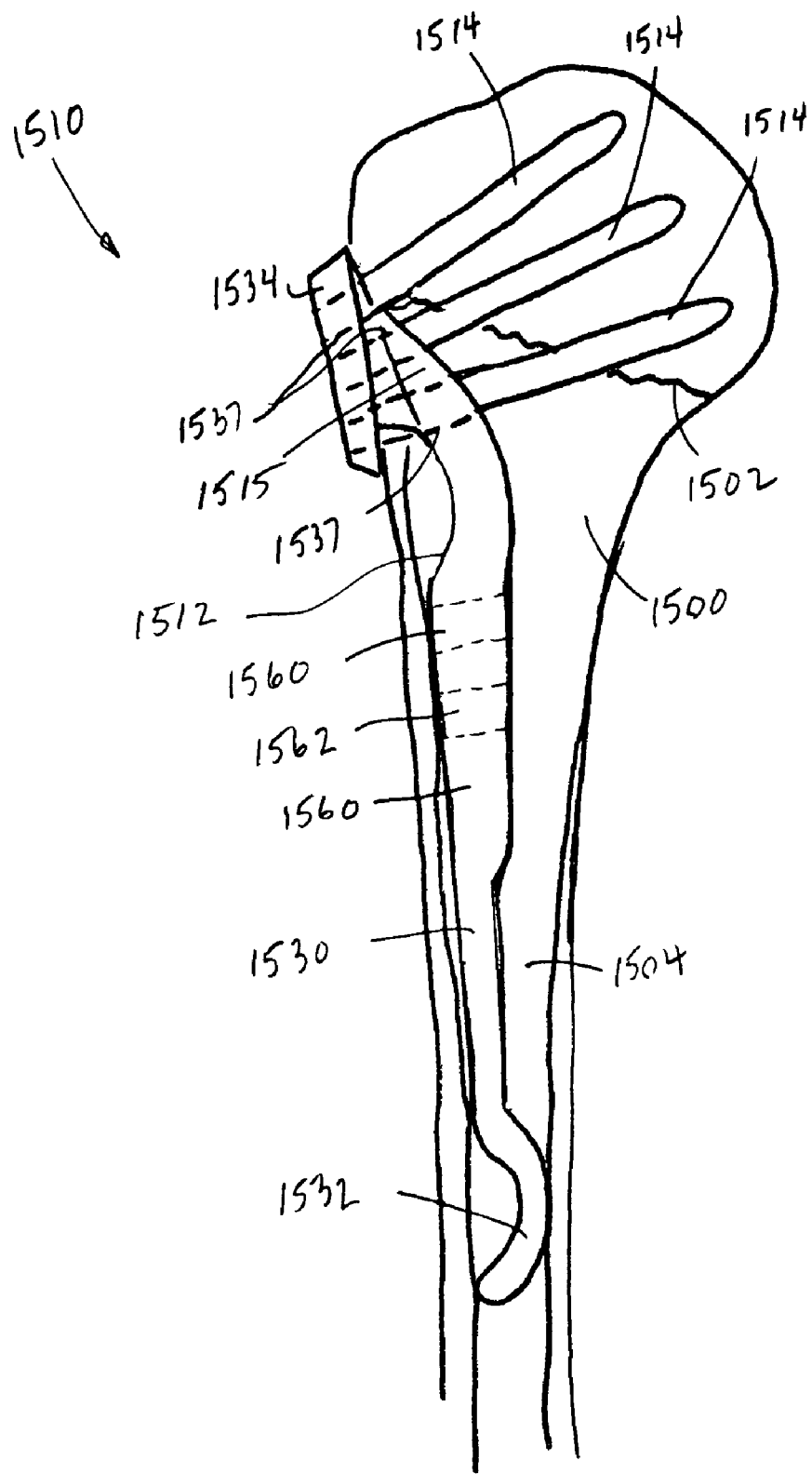
FIG. 31 is a schematic section view of a nail-plate embodiment of a proximal humeral fixation system according to the invention.

Referring to FIG. 31, another embodiment of a humeral fracture fixation system 1510 is shown coupled to a shoulder 1500, with the posts 1514 extending across a fracture 1502. The system 1510 includes a device 1512 having a plate-like head portion 1534, a neck 1515, and a shaft 1530. The neck 1515 of the device is attached to the head portion 1534 so as to seat intrafocally just below the fracture 1502. As a result of the forward location of the neck 1515, one or more of the post holes 1537 in the plate-like head portion 1534 extends through the neck 1515. The post holes 1537 are preferably axially angularly offset relative to each other. In contrast to the prior embodiments, the shaft portion 1530 of the device 1512 defines an intramedullary nail sized to be inserted intrafocally (through the fracture) and then be received within the medullary canal of the proximal humerus. Thus, the device 1512 is a "nail-plate." The shaft portion 1530 preferably extends from a lower central location of the head portion 1534, in distinction from the inferior end thereof. The shaft portion 1530 preferably tapers to facilitate entry into the medullary canal and terminates in a smooth bend 1532 which facilitates intrafocal entry of the end of the shaft, and further insertion into the medullary canal 1504. In addition, the shaft portion 1530 is preferably offset relative to the head portion 1534, as the shaft portion 1530 is intended to reside within the bone and the head portion 1534 is intended to reside on the surface of the bone. Holes 1560, 1562 are provided in the shaft portion for receiving fasteners. The holes 1560, 1562 are preferably threaded, and thus adapted to receive machine screws which can pull the shaft portion 1530 against the cortex of the bone. Alternatively non-threaded holes may be used, and standard cortical screws provided to couple the shaft to the humeral cortex. "Nail-plates" are described in more detail in co-owned U.S. Ser. No. 10/315,787, filed Dec. 10, 2002, which is hereby incorporated by reference herein in its entirety.

There have been described and illustrated herein embodiments of fracture fixation systems and methods of stabilizing a fracture, particularly of the humerus. While particular embodiments of the invention have been described, it is not intended that the invention be limited thereto, as it is intended that the invention be as broad in scope as the art will allow and that the specification be read likewise. Thus, while the preferred embodiments are for humeral fracture fixation systems, it is appreciated that the system is well adapted to bone fractures of any articular surface having a convex shape. Thus, the system of the invention could similarly be used to treat a fracture of the femoral head. In such variation, the angle between the head and shaft portions may be different so that the head portion properly seats on the anatomy. In addition, while a particular number of posts and cortical screws have been disclosed in relation to particular embodiments, it will be understood that only one post is required, and fewer or more cortical screw holes can be provided and/or screws can be used. Furthermore, while cortical screws are disclosed for coupling the shaft portion to the bone, other fasteners can likewise be used. Moreover, while the terms 'posts' and 'pegs' have been used to described particular elements of the invention, it is understood that such terms are used as a matter of convenience, and are not intended to confer particular structure when used in the claims. Thus, what is referred to as a 'post' is intended to broadly read on any shaft-like fastener coupled to the plate. Also, what is referred to as a 'peg' is intended to broadly read on any shaft-like element which extends in transverse relation one of the posts and is (i) coupled to such post and/or (ii) extends through a transverse hole formed within the post. Thus, the peg may be a screw, a non-threaded rod, a K-wire, etc.

Furthermore, while left-hand humeral plates are shown, it is recognized that right-hand humeral plates are generally mirror-images of the illustrated left-hand plates. Moreover, while the system has been described for use with respect to fractures, it is appreciated that it may also be used in the treatment of osteotomies and non-unions of the proximal humerus and other bones having an articular surface with a convex shape. It will therefore be appreciated by those skilled in the art that yet other modifications could be made to the provided invention without deviating from its scope as claimed.

What is claimed is:

1. A plate for a bone fracture fixation system, comprising:
a head portion and shaft portion, a bone contacting first surface, and an opposite second surface, said shaft portion defining a longitudinal axis,
said head portion provided with six post holes and a K-wire hole substantially smaller in diameter than any of said six post holes and located at a center relative to an arrangement of said six post holes, said K-wire hole having a longitudinally central axis,
four of said six post holes being located at the corners of a rectangular quadrilateral and having fixed axes that are divergent in a first direction parallel with said longitudinal axis and divergent in a second direction perpendicular to said first direction such that when said plate is positioned on the bone said fixed axes of said four post holes extend beneath said first surface of said plate and are limited to only diverge in said first and second directions into the bone, and
and two of said six post holes being located outside said quadrilateral along an axis parallel to said axis which laterally bisects said rectangular quadrilateral, said two post holes having fixed axes that are convergent toward a portion of said central axis of said K-wire hole such that when said plate is positioned on the bone said fixed axes of said two post holes extend beneath said first surface of said plate and into the bone.

2. A plate according to claim 1, wherein:
said head portion is angled relative to said shaft portion such that said head portion extends through a different plane than said shaft portion, said head portion has a curved posterior side and a straight anterior side, and said shaft portion has a straight anterior side, such that said anterior sides of said head and shaft portions define a co-extensive straight line.

3. A plate according to claim 1, further comprising:

a plurality of suture supports arranged about said head portion, said suture supports being elevated relative to said lower surface of said head portion.

4. A plate according to claim 3, wherein:

said suture supports are discrete from each other.

5. A plate according to claim 4, wherein:

said suture supports are substantially radially arranged about a point on said head portion.

6. A plate according to claim 1, wherein:

said shaft portion has a bone contacting first surface, an opposite second surface, a thickness between said first and second surface, and a width transverse to said thickness, wherein said width is greater than said thickness, and a plurality of screw holes extending completely through said thickness of said plate.

* * * * *